(12) United States Patent
Prakash et al.

(10) Patent No.: US 11,406,676 B2
(45) Date of Patent: *Aug. 9, 2022

(54) THERAPEUTIC VIRAL MICROPARTICLES FOR PROMOTING STENT BIOFUNCTIONALITY AND WOUND HEALING IN VERTEBRATE INDIVIDUALS

(71) Applicant: MANGOGEN PHARMA INC., Laval (CA)

(72) Inventors: Satya Prakash, Broassard (CA); Arghya Paul, Longueuil (CA); Dominique Shum-Tim, Beaconsfield (CA)

(73) Assignee: MANGOGEN PHARMA INC., Laval (CA)

(*) Notice: Subject to any disclaimer, the term of this patent is extended or adjusted under 35 U.S.C. 154(b) by 13 days.

This patent is subject to a terminal disclaimer.

(21) Appl. No.: 16/105,498

(22) Filed: Aug. 20, 2018

(65) Prior Publication Data

US 2019/0111092 A1 Apr. 18, 2019

Related U.S. Application Data

(63) Continuation of application No. 14/783,832, filed as application No. PCT/CA2014/050369 on Apr. 11, 2014, now Pat. No. 10,092,607.

(60) Provisional application No. 61/811,203, filed on Apr. 12, 2013.

(51) Int. Cl.
| | | |
|---|---|---|
| *A61K 35/76* | (2015.01) | |
| *A61L 31/16* | (2006.01) | |
| *A61L 31/10* | (2006.01) | |
| *A61K 38/19* | (2006.01) | |
| *C12N 7/00* | (2006.01) | |
| *A61K 9/50* | (2006.01) | |
| *A61K 38/36* | (2006.01) | |
| *A61L 31/12* | (2006.01) | |
| *A61L 31/14* | (2006.01) | |
| *A61K 48/00* | (2006.01) | |

(52) U.S. Cl.
CPC ............ *A61K 35/76* (2013.01); *A61K 9/5031* (2013.01); *A61K 9/5089* (2013.01); *A61K 38/19* (2013.01); *A61K 38/36* (2013.01); *A61K 38/363* (2013.01); *A61L 31/10* (2013.01); *A61L 31/125* (2013.01); *A61L 31/148* (2013.01); *A61L 31/16* (2013.01); *C12N 7/00* (2013.01); *A61K 48/00* (2013.01); *A61L 2300/414* (2013.01); *A61L 2300/418* (2013.01); *A61L 2300/622* (2013.01); *A61L 2430/34* (2013.01); *C12N 2710/14032* (2013.01); *C12N 2710/14043* (2013.01); *C12N 2710/14143* (2013.01)

(58) Field of Classification Search
CPC ...... A61K 35/76; A61K 9/5031; A61K 38/19; A61L 31/16
See application file for complete search history.

(56) References Cited

U.S. PATENT DOCUMENTS

| | | | |
|---|---|---|---|
| 6,413,735 B1 | 7/2002 | Lau | |
| 10,092,607 B2 * | 10/2018 | Prakash | ............... A61K 9/5031 |
| 2006/0287234 A1 * | 12/2006 | Breen | ................ A61K 38/1866 |
| | | | 514/8.1 |
| 2007/0066552 A1 | 3/2007 | Clarke et al. | |

OTHER PUBLICATIONS

Theses and dissertations published in 2012—McGill—Érudit; https://www.erudit.org/en/theses/mcgill/2012/?page=14; accessed Oct. 19, 2020; pp. 1-7 (Year: 2020).*
Grassi et al.; Comparison between recombinant baculo- and adenoviral-vectors as transfer system in cardiovascular cells; Archives of Virology; (2006); 151: 255-271 (Year: 2006).*
Paul, "Novel Biotherapeutic Devices: Studies With Stem Cells, Nanohybrid Viral Vectors and Microcapsules for Cardiovascular Applications" A Thesis Submitted To McGill University, Jan. 2012.
Li, Office Action for Chinese Application 201480031705.8, dated Apr. 13, 2018.
Sitch, Examination Report for EP 14783183.8 dated Sep. 27, 2017.
Anonymous, "Microparticle", Wikipedia, https://en.wikipedia.org/wiki/Microparticle, Retrieved on Oct. 4, 2016, 16:38, 4 pages.
Beer, Steven, J., et al., "Extended release of adenovirus from polymer microspheres: potential use in gene therapy or brain tumors", Advanced Drug Delivery Reviews, vol. 27, (1997), pp. 59-66.

(Continued)

*Primary Examiner* — Antonio Galisteo Gonzalez

(74) *Attorney, Agent, or Firm* — Wilson Sonsini Goodrich & Rosati

(57) ABSTRACT

The present disclosure provides viral microparticles comprising genetically-engineered baculoviruses (at least partially) embedded in a polymeric matrix for the local delivery of therapeutic nucleic acid molecules to the cells of a vertebrate individual (optionally in combination with a medical implant such as vascular stent platform). The viral microparticles are especially useful for promoting the healing of a wound as well as the repair of a blood vessel and prevent pathological scarring. Also provided herein are processes for making the viral microparticles, pharmaceutical compositions comprising viral microparticles as well as supports comprising the viral microparticles for the locating the viral microparticles in a wound or in the vicinity of a wound.

Figure 1A:
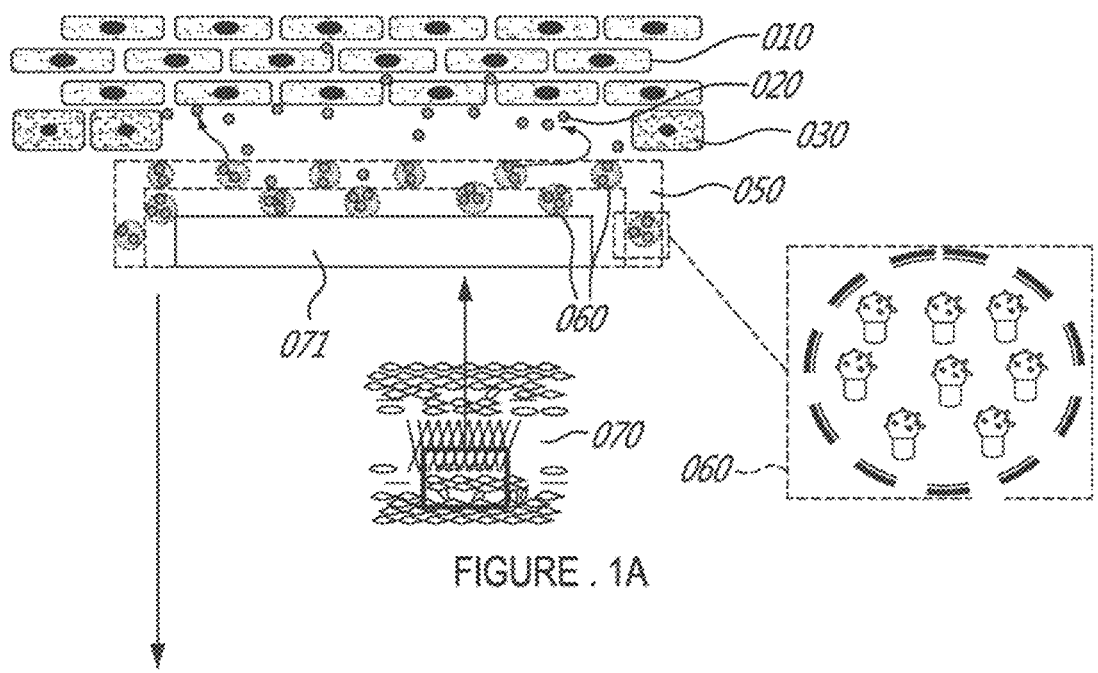
Figure 1B:
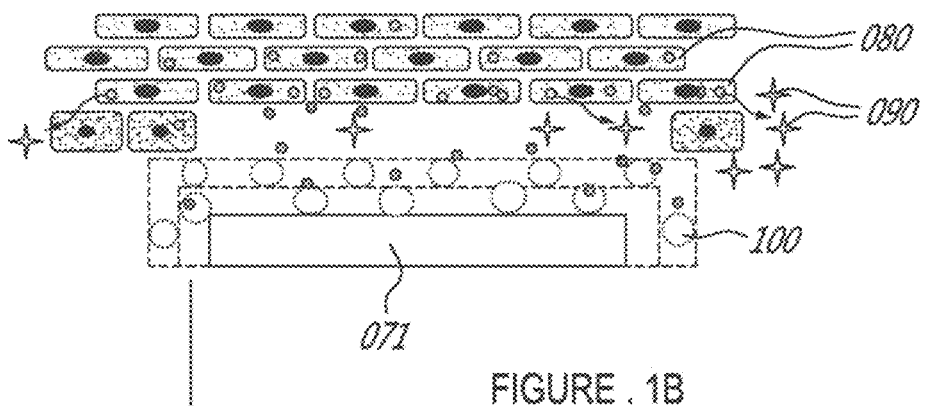
Figure 1C:
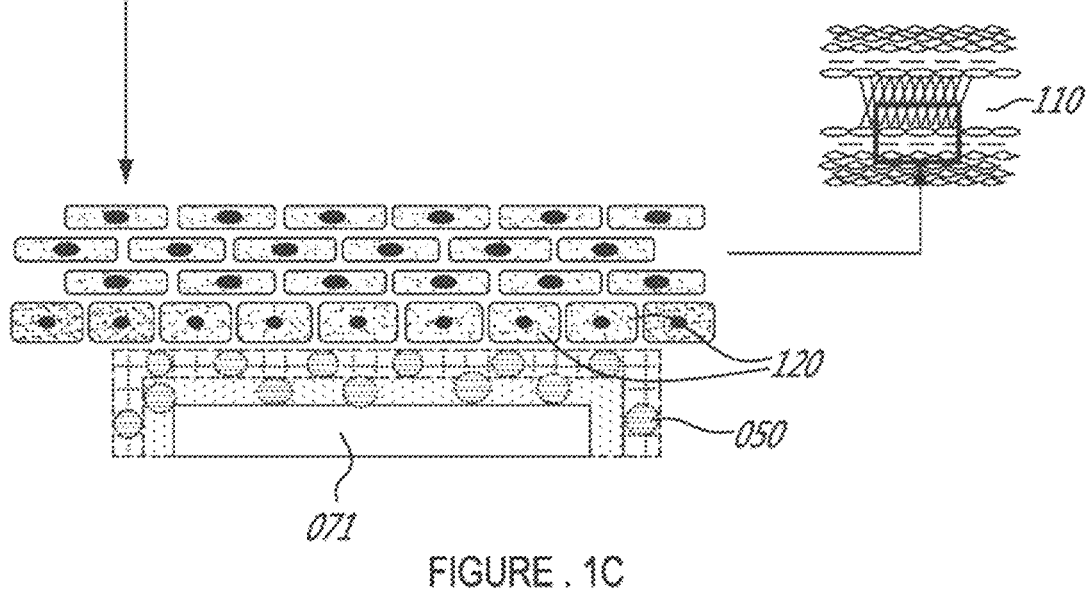
Figure 1D:
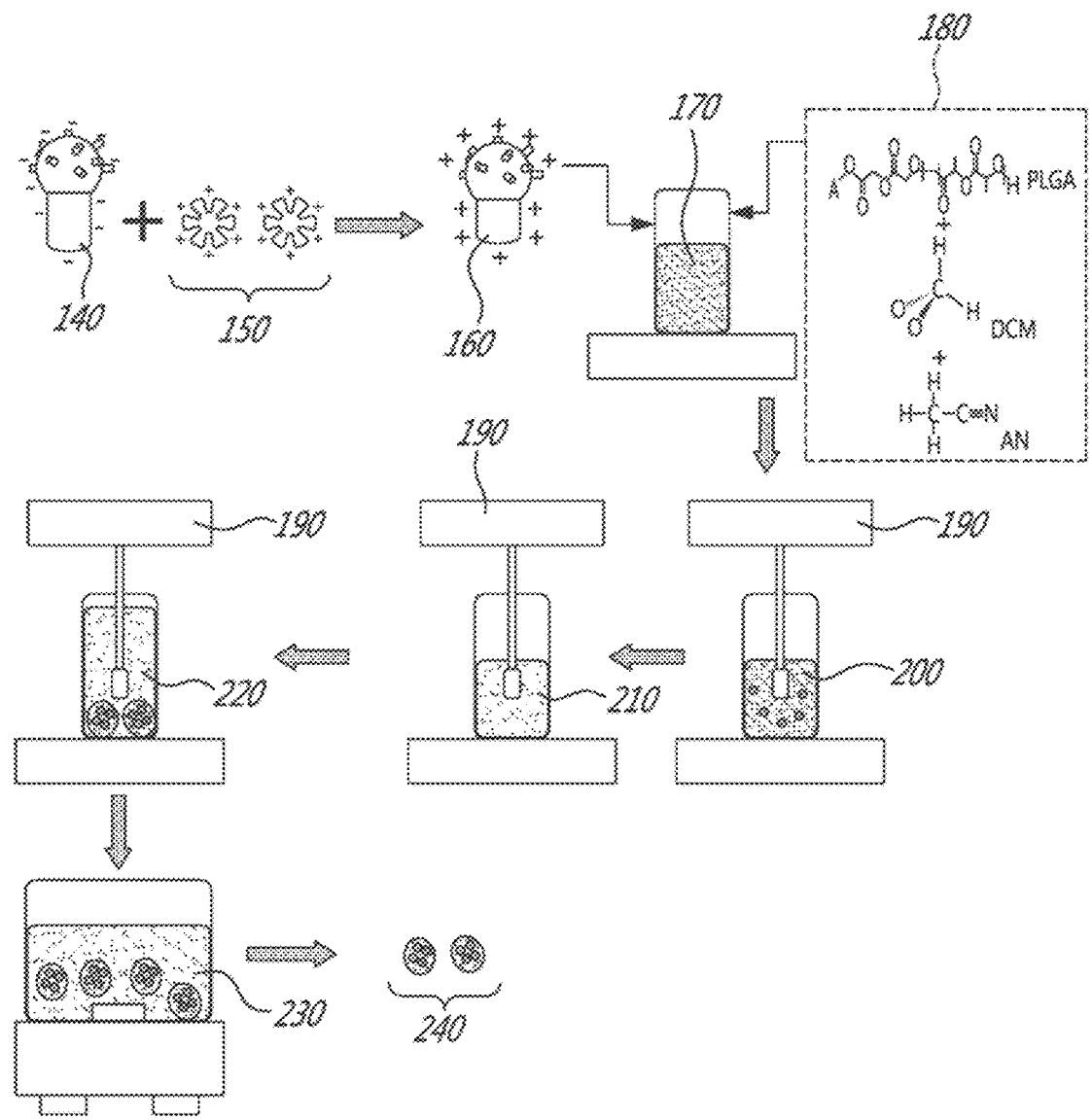

20 Claims, 14 Drawing Sheets
Specification includes a Sequence Listing.

(56) References Cited

OTHER PUBLICATIONS

Paul, A., et al., "Bioactive baculovirus naohybrids for stent based rapid vascular re-endothelialization", Science Report, No. 3, Article No. 2366, (2013), 9 pages.

Kang, Yi, et al., "Polyethylenimine coating to produce serum-resistant baculoviral vectors for in vivo gene delivery", Biomaterials, vol. 30, (2009), pp. 5767-5774.

Stitch, David, "Communication pursuant to Rule 164(1) EPC and Supplementary Partial European Search Report under Rule 164, paragraph 1 of the European Patent Convention", European Patent Office, European Patent Application No. EP 14 78 3183, Transmitted Nov. 2, 2016, Search Completed Oct. 5, 2016, 13 pages.

Beer et al., "Poly (lactic-glycolic) acid copolymer encapsulation of recombinant adenovirus reduces immunogenicity in Vivo" Gene Therapy, 1998, v 5, p. 740-746.

Paul et al., "PAMAM Dendrimer-Baculovirus Nanocomplex for Microencapsulated Adipose Stem Cell-Gene Therapy: In Vitro and in Vivo Functional Assessment" Mol. Pharmaceutics 2012, v 9, p. 2479-2488.

Paul et al., "The attenuation of restenosis following arterial gene transfer using carbon nanotube coated stent incorporating TAT/DNAAng1+Vegf nanoparticles." Biomaterials, 2012, v 33, p. 7655-7664.

Hiltunen et al., "Intravascular Adenovirus-1\lediated VEGF-C Gene rfransfer Reduces Neointima Formation in Balloon-Denuded Rabbit Aorta" Downloaded from http://circ.ahajournals.org/ on Jan. 10, 2016.

Pilon, International Search Report for PCT/CA2014/050369 dated Jul. 11, 2014.

Li, Second Office Action Action for Chinese Patent Application CN 201480031705.8 dated Nov. 16, 2018.

Fishbein, I et al. "Stent-based delivery of adeno-associated viral vectors with sustained vascular transduction and iNOS-mediated inhibition of in-stent restenosis." Gene therapy vol. 24,11 (2017): 717-726. doi:10.1038/gt.2017.82.

Jiang, J et al. "IRX1 influences peritoneal spreading and metastasis via inhibiting BDKRB2-dependent neovascularization on gastric cancer." Oncogene vol. 30,44 (2011): 4498-508. doi:10.1038/onc.2011.154.

Kornowski R. et al., "In-stent restenosis: contributions of inflammatory responses and arterial injury to neointimal hyperplasia", J Am Coll Cardiol, Jan. 1998;31(1):224-30. doi:10.1016/s0735-1097(97)00450-6. PMID: 9426044.

Kumar, Neeraj et al. "Preventive, Diagnostic and Therapeutic Applications of Baculovirus Expression Vector System." Trends in Insect Molecular Biology and Biotechnology 163-191. Nov. 16, 2017,doi:10.1007/978-3-319-61343-7_9.

Lee J et al., "Effect of formulation and processing variables on the characteristics of microspheres for water-soluble drugs prepared by w/o/o double emulsion solvent diffusion method", Int J Pharm. Feb. 25, 2000;196(1):75-83. doi: 10.1016/s0378-5173(99)00440-8. PMID: 10675709.

Matthews C. et al., "Poly-L-lysine improves gene transfer with adenovirus formulated in PLGA microspheres", Gene Ther. Sep. 1999;6(9):1558-64.doi: 10.1038/sj.gt.3300978. PMID: 10490765.

Mok H. et al., "Microencapsulation of PEGylated adenovirus within PLGA microspheres for enhanced stability and gene transfection efficiency", Pharmaceutical Research Dec. 2007:24(142263-9. doi: 10.1007/s11095-007-9441-y. Epub Oct. 11, 2007. PMID: 17929147.

Newman, K D et al. "Adenovirus-mediated gene transfer into normal rabbit arteries results in prolonged vascular cell activation, inflammation, and neointimal hyperplasia." The Journal of clinical investigation vol. 96,6 (1995): 2955-65. doi:10.1172/JCI118367.

Paul A. et al., "A nanobiohybrid complex of recombinant baculovirus and Tat/DNA nanoparticles for delivery of Ang-1 transgene in myocardial infarction therapy", Biomaterials. Nov. 2011;32(32):8304-18. doi:10.1016/j.biomaterials.2011.07.042. Epub Aug. 15, 2011. PMID: 21840594.

Schwartz RS, et al., "Restenosis after balloon angioplasty. A practical proliferative model in porcine coronary arteries", Circulation, Dec. 1990 82:2190-2200.

Schwartz RS, et al., "Restenosis and the proportional neointimal response to coronary artery injury: results in a porcine model", J Am Coll Cardiol. Feb. 1992;19(2):267-74. doi: 10.1016/0735-1097(92)90476-4.PMID: 1732351.

Sharif F, et al., "Gene-eluting scents: Adenovirus-mediated delivery of eNOS to the blood vessel wall accelerates re-endothelialization and inhibits restenosis", Molecular Therapy Oct. 2008,16(10).1674-90.

Sharif F, et al., "Gene-eluting stents: comparison of adenoviral and adeno- associated viral gene delivery to the blood vessel wall in vivo", Hum Gene Ther. Jul. 2006;17(7):741-50. doi:10.1089/hum.2006.17.741. PMID: 16839273.

Welt FG, et al., "Neutrophil, not macrophage, infiltration precedes neointimal thickening in balloon-injured arteries", Arterioscler Thromb Vasc Biol. Dec. 2000;20(12):2553-8. doi: 10.1161/01.atv.20.12.2553. PMID:11116052.

Worsey MJ, et al., " Endovascular Canine Anastomotic Stenting", Journal of Surgical Research Jan. 1993;54(1):29-33.

Tani, Hideki et al. "In vitro and in vivo gene delivery by recombinant baculoviruses." Journal of virology vol. 77,18 (2003): 9799-808. doi:10.1128/jvi.77.18.9799-9808.200.

\* cited by examiner

Figure 2A:
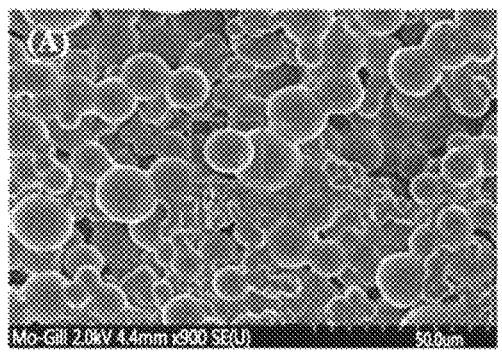
Figure 2A:
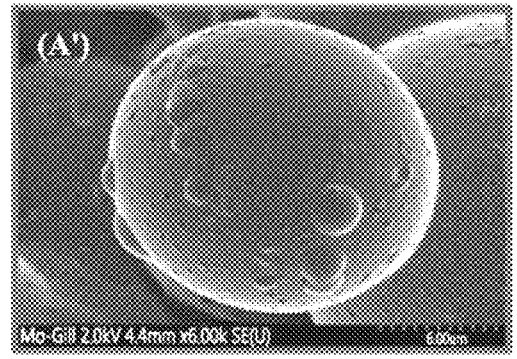
Figure 2C:
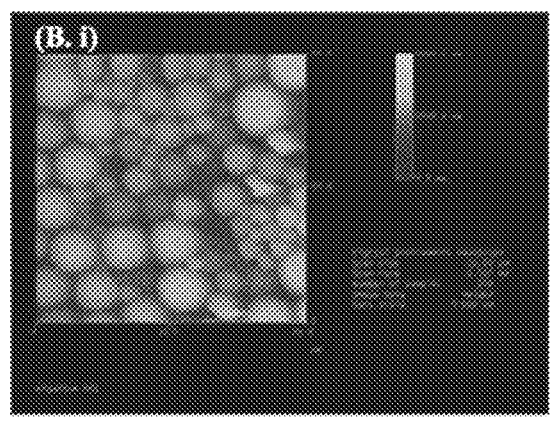
Figure 2C:
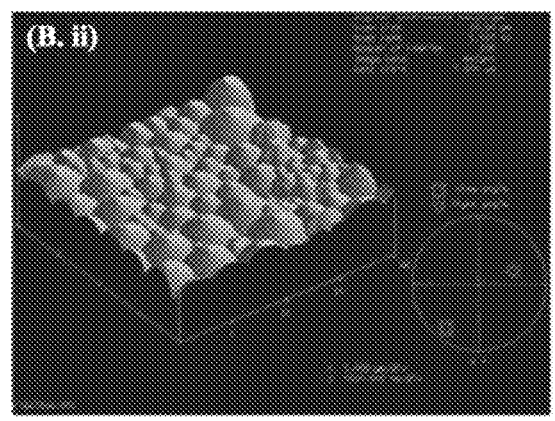
Figure 2C:
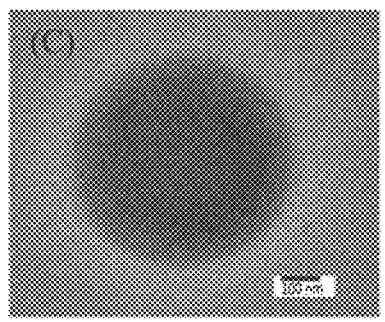
Figure 2D:
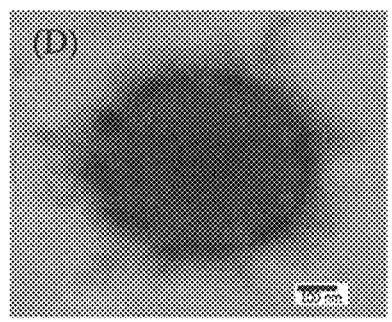
Figure 2E:
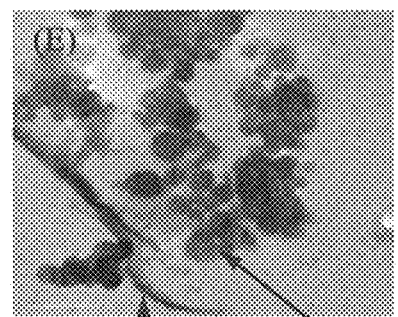

FIGURE. 2B.i

FIGURE. 2B.ii

Outer surface — Entrapped virus

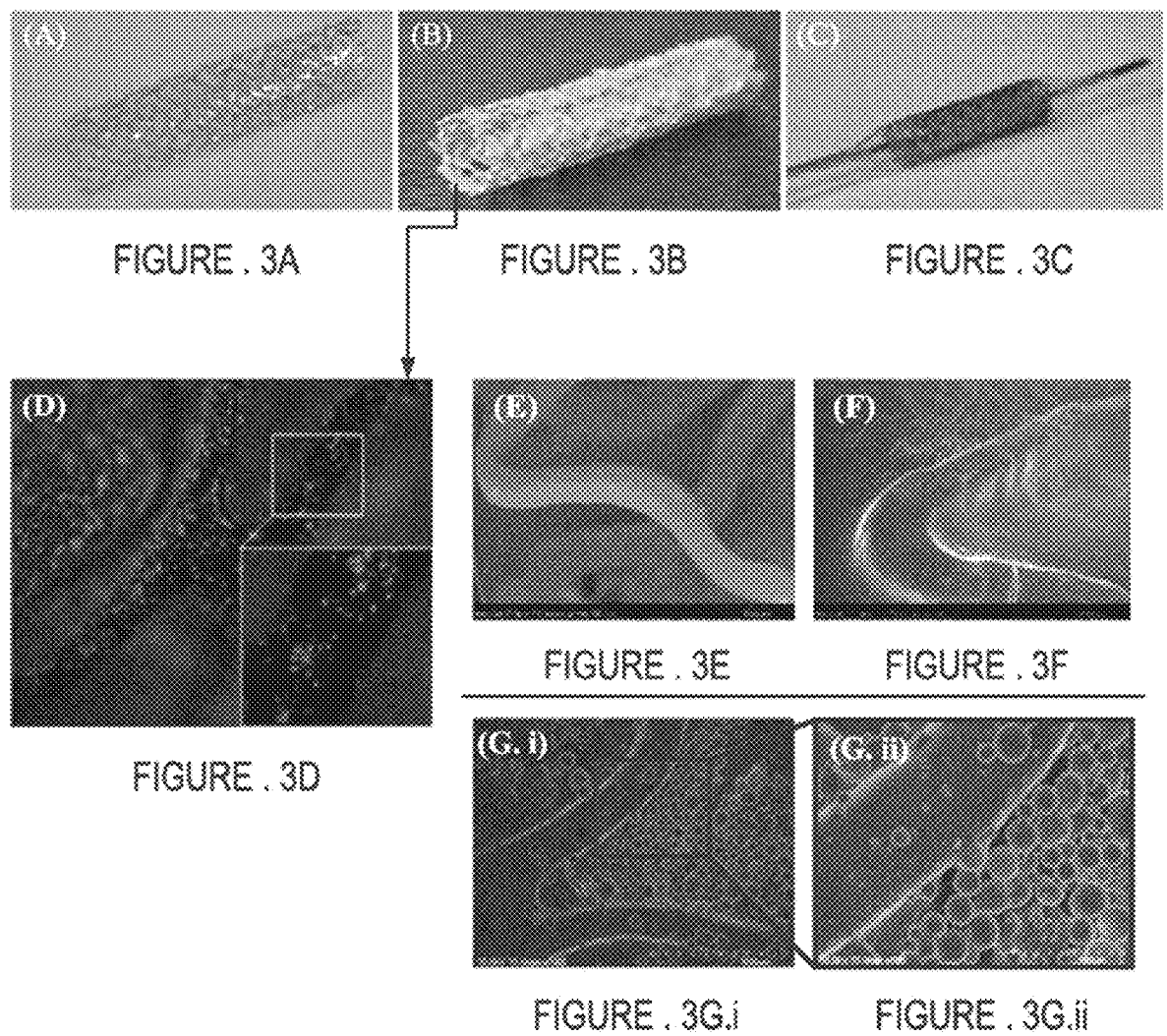
FIGURE. 3A  FIGURE. 3B  FIGURE. 3C
FIGURE. 3D  FIGURE. 3E  FIGURE. 3F
FIGURE. 3G.i  FIGURE. 3G.ii
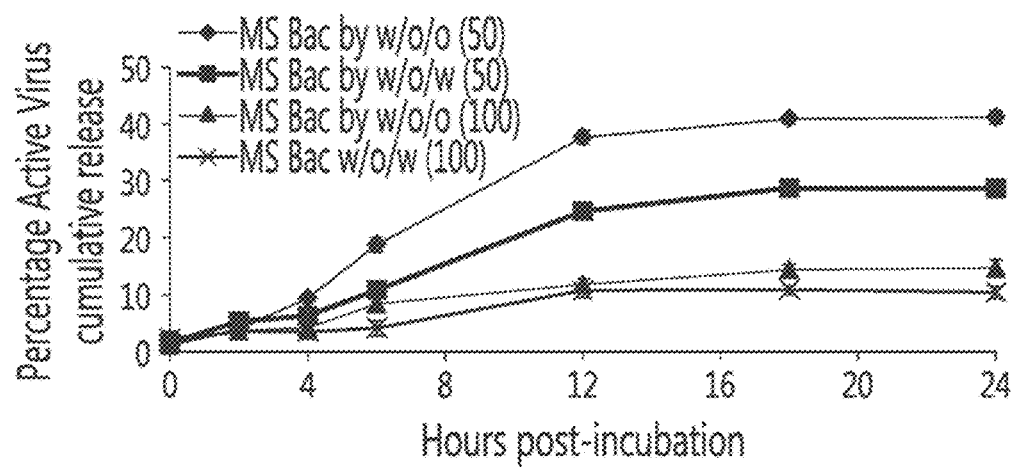
FIGURE. 3H

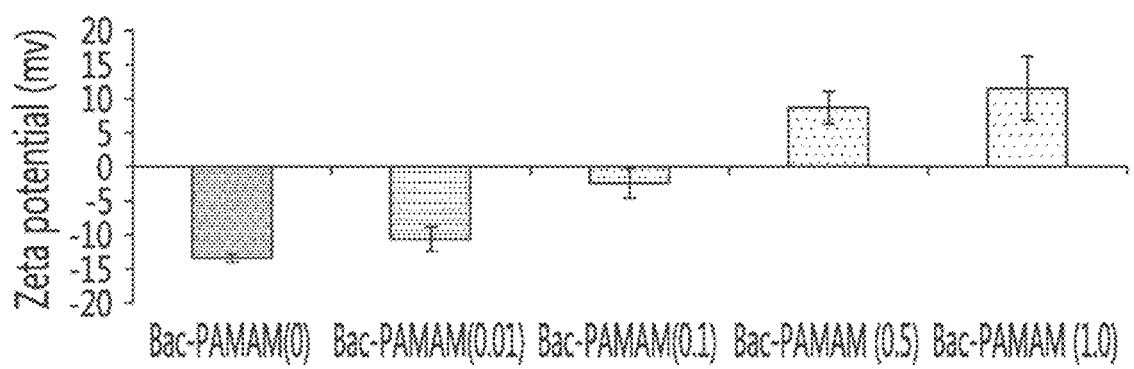
FIGURE. 4A
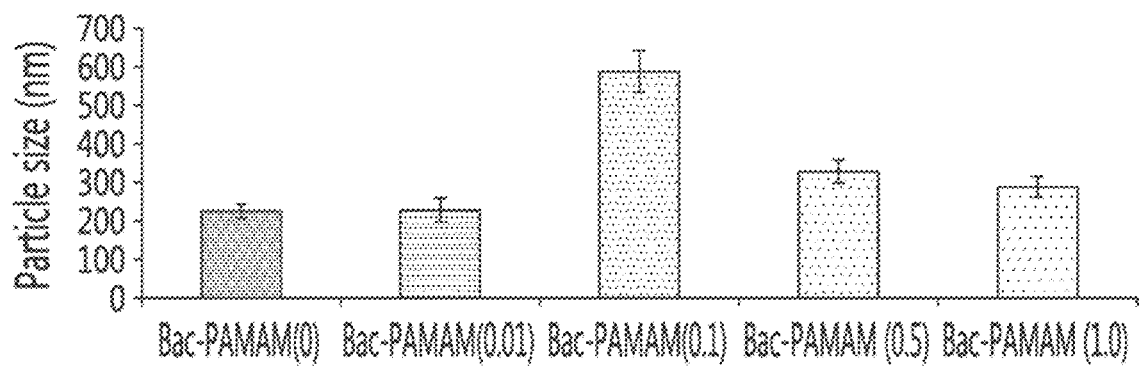
FIGURE. 4B
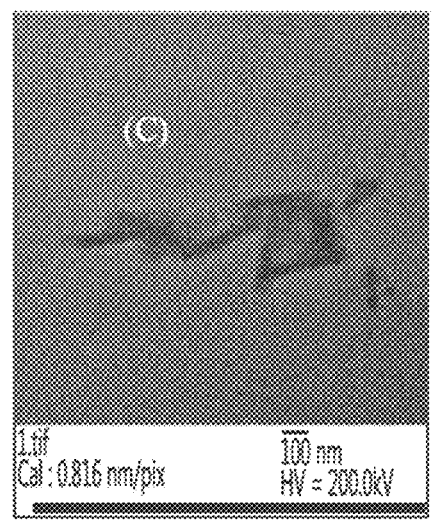 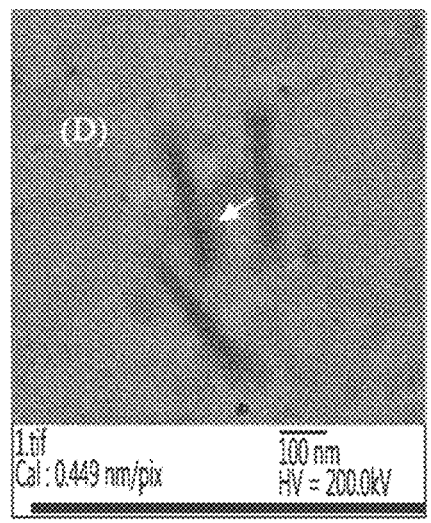
FIGURE. 4C　　　　　　FIGURE. 4D

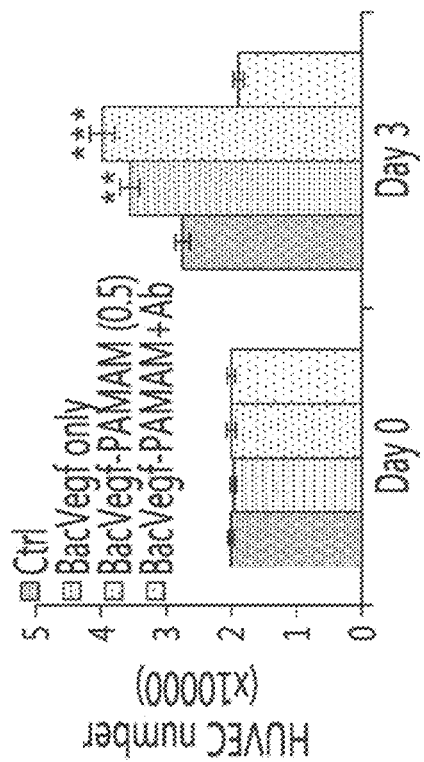
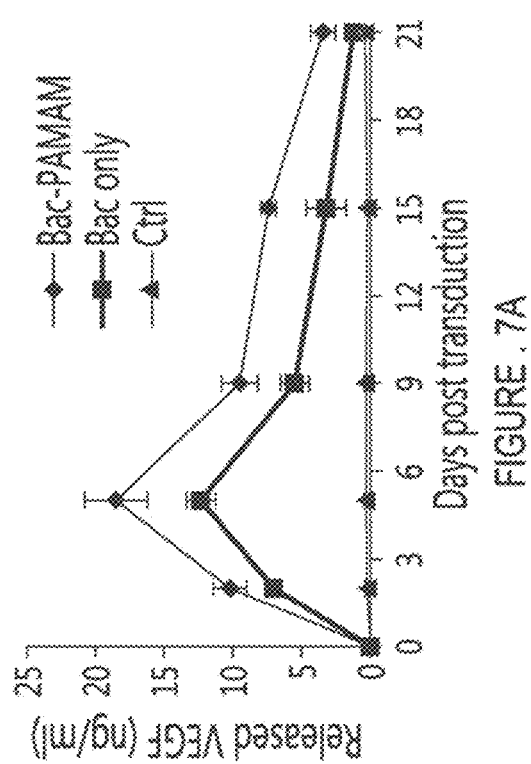
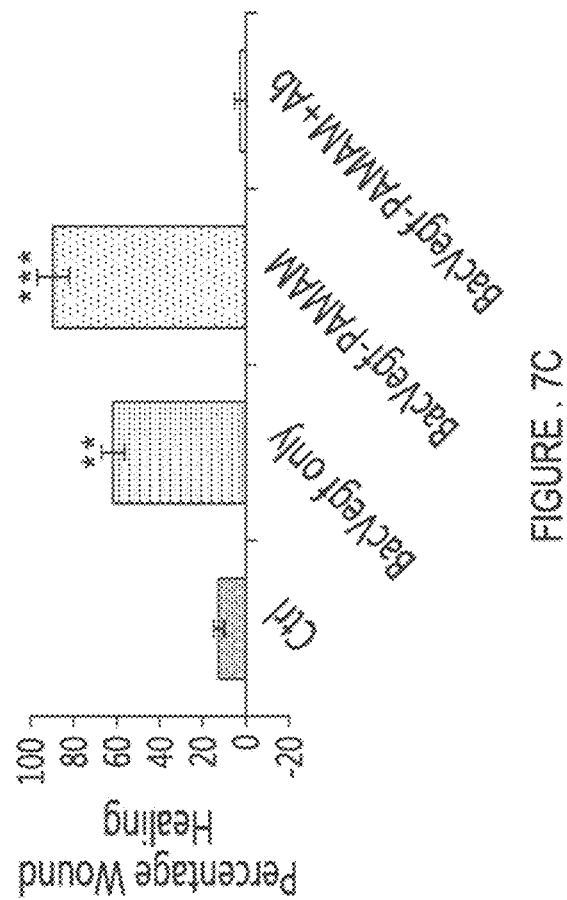
FIGURE. 7A
FIGURE. 7B
FIGURE. 7C

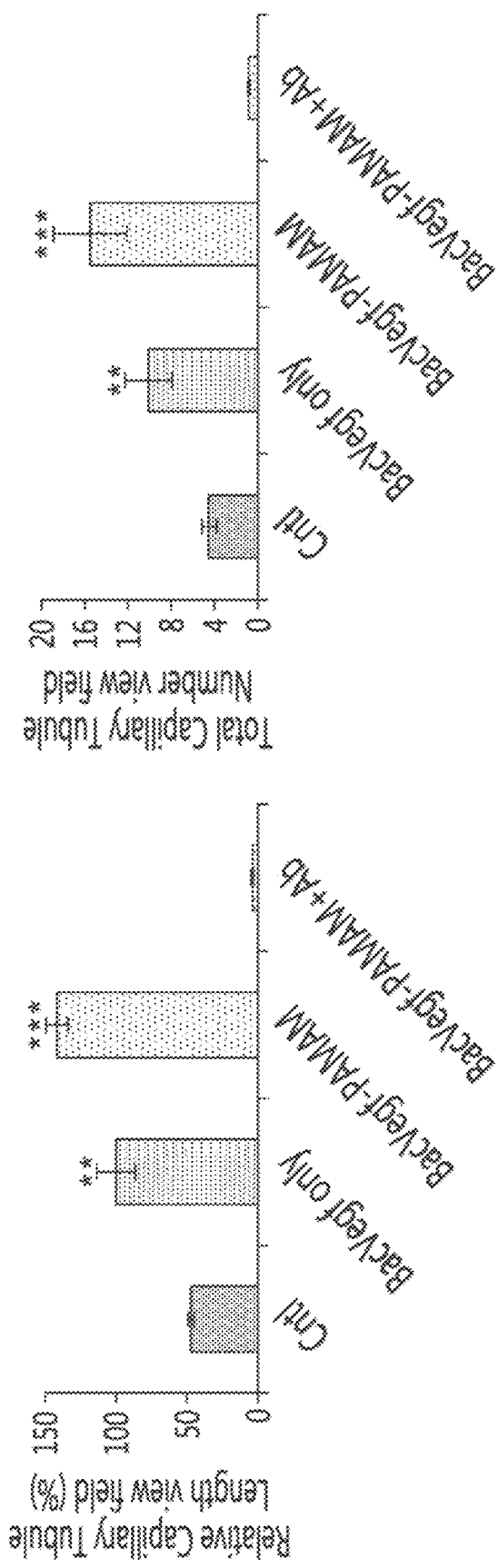
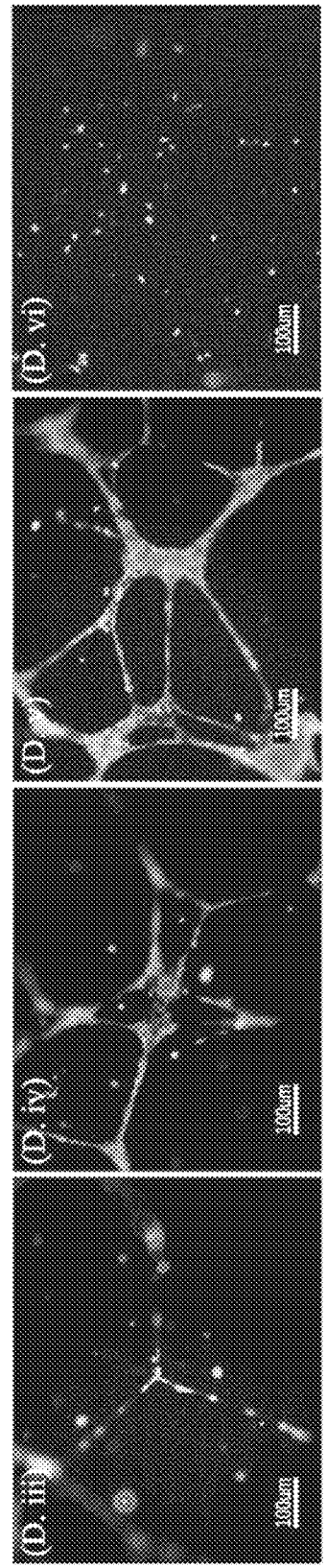
FIGURE. 7D.i  FIGURE. 7D.ii
FIGURE. 7D.iii  FIGURE. 7D.iv  FIGURE. 7D.v  FIGURE. 7D.vi FIGURE. 8A.iii FIGURE. 8A.i FIGURE. 8A.ii FIGURE. 8C.i FIGURE. 8C.ii FIGURE. 8C.iii FIGURE. 8C.iv

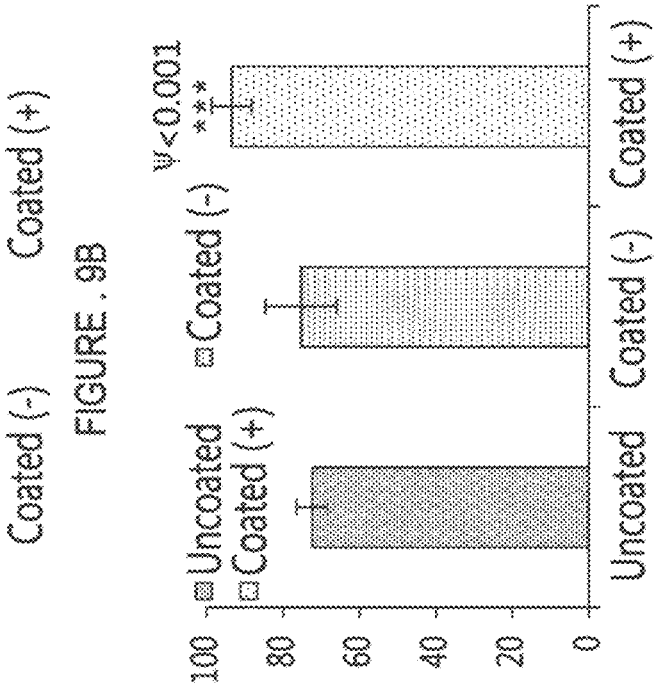
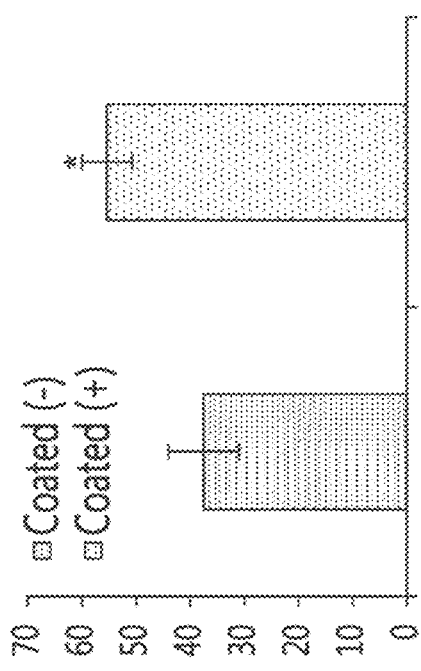
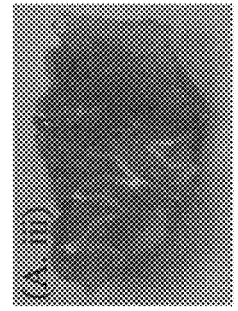
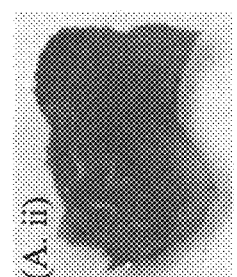
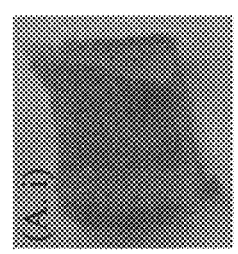
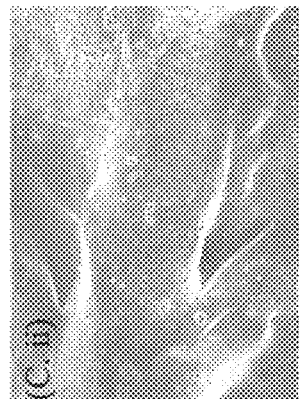
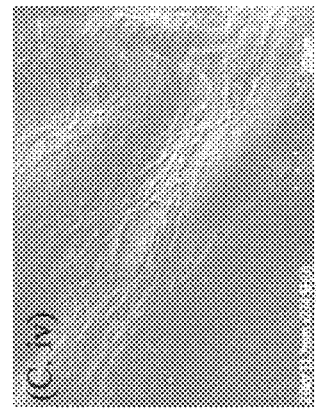
FIGURE. 9A.i  FIGURE. 9A.ii  FIGURE. 9A.iii
FIGURE. 9B
FIGURE. 9C.i  FIGURE. 9C.ii
FIGURE. 9C.iii  FIGURE. 9C.iv
FIGURE. 9D

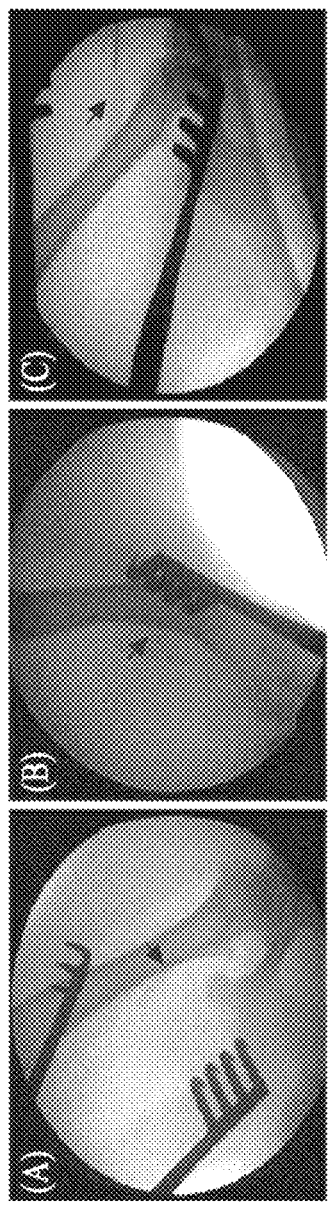
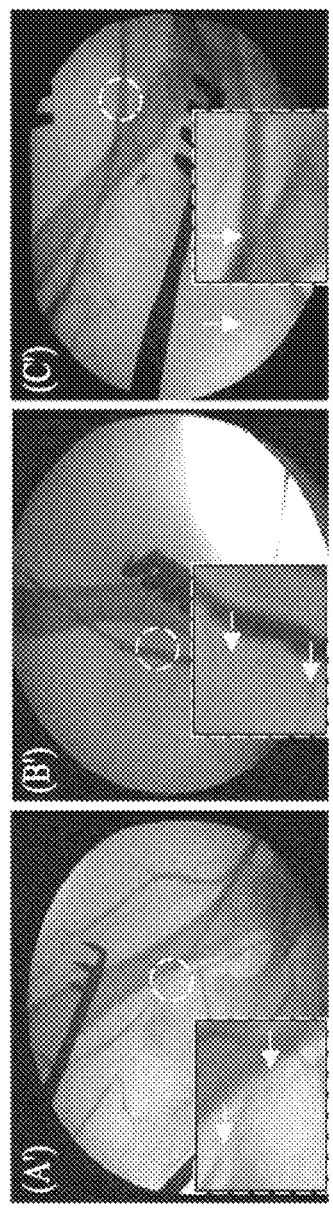
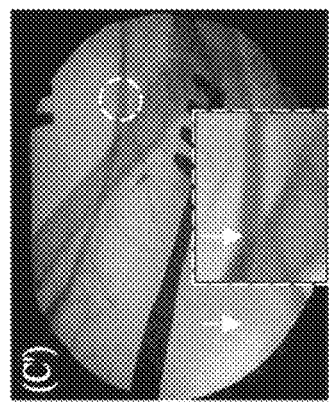
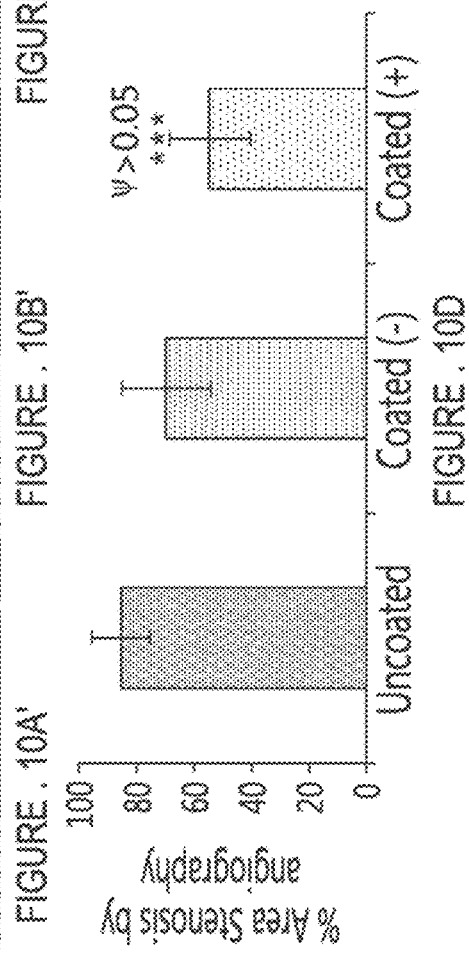

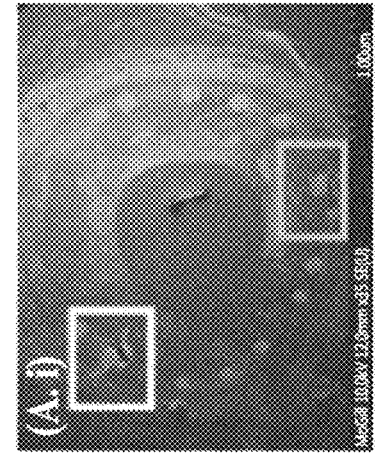
FIGURE. 11A.i
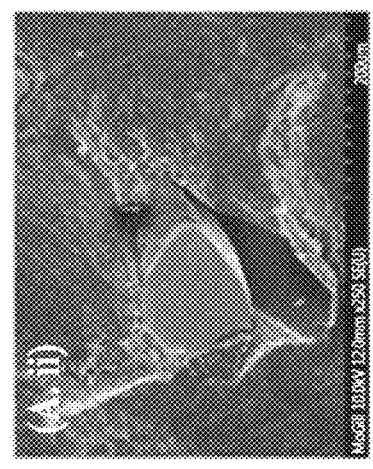
FIGURE. 11A.ii
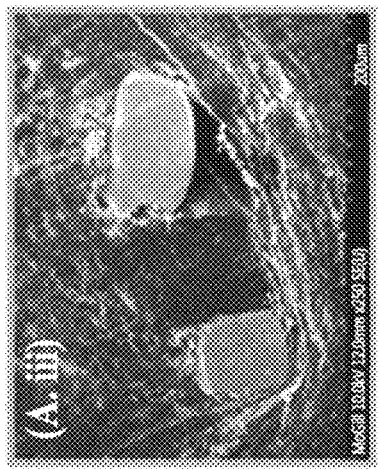
FIGURE. 11A.iii
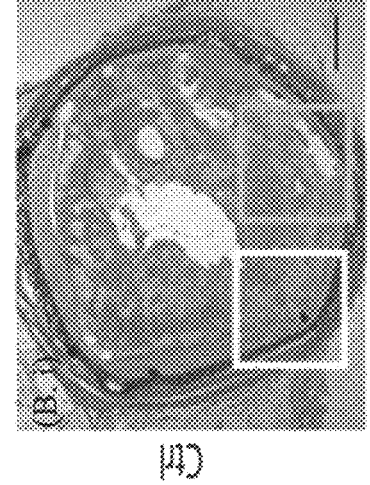
FIGURE. 11B.i
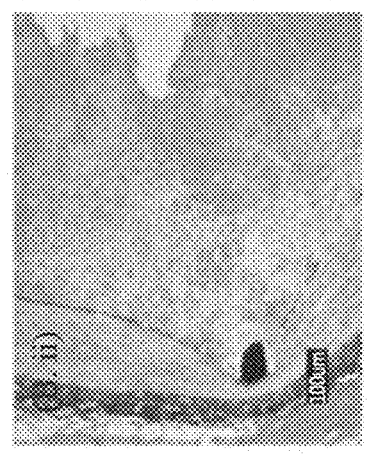
FIGURE. 11B.ii
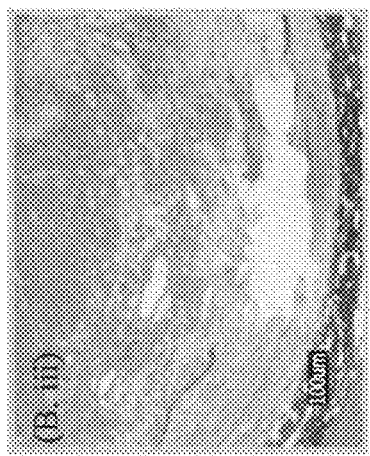
FIGURE. 11B.iii

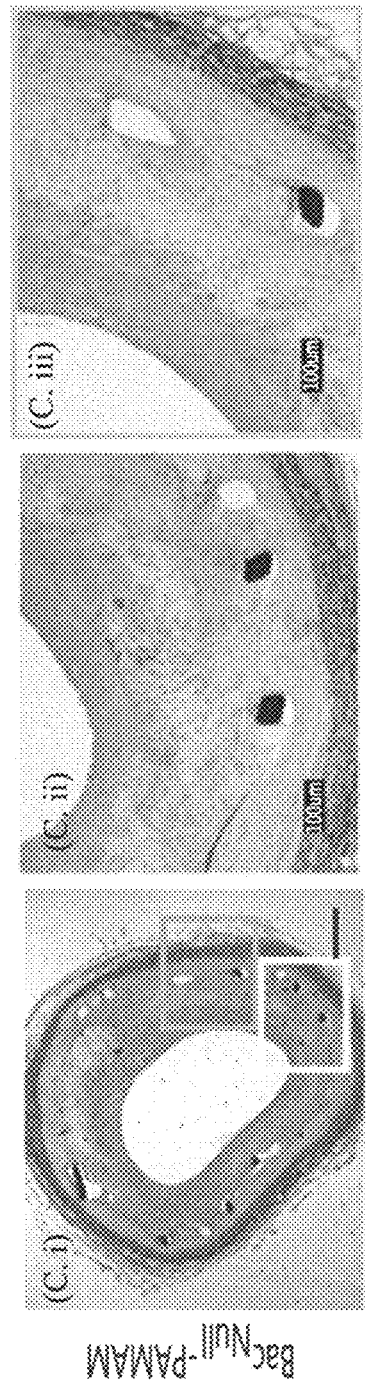
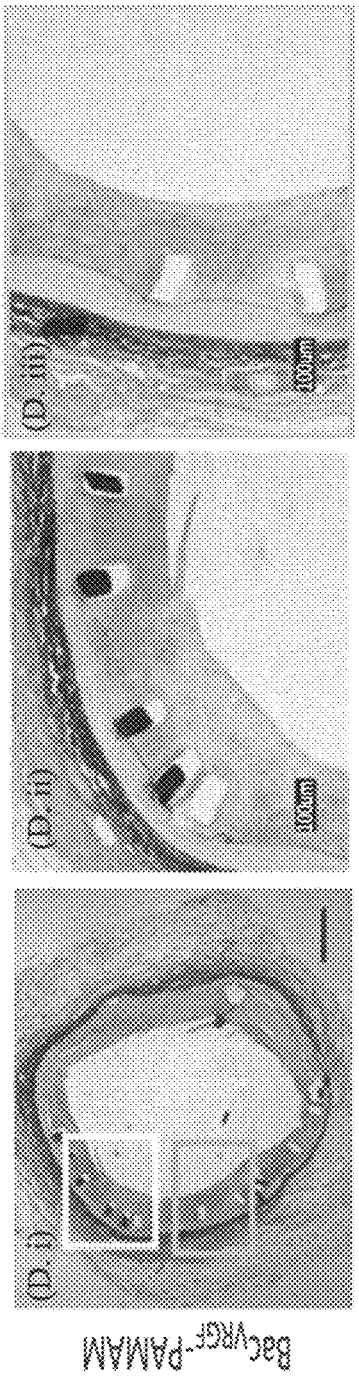
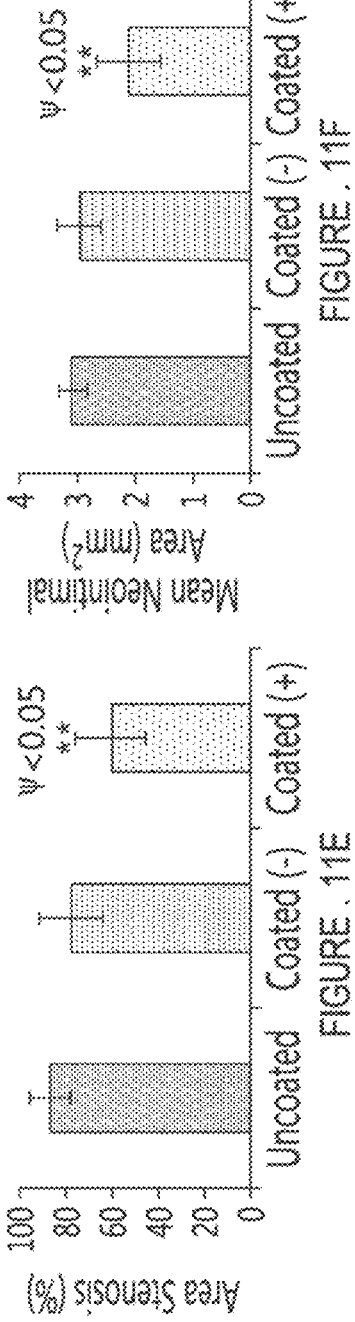

SEQUENCE LISTING

<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: Oligonucleotide

<400> SEQUENCE: 1
cttgccttgc tgctctacct cc                                           22

<210> SEQ ID NO 2
<211> LENGTH: 22
<212> TYPE: DNA
<213> ORGANISM: Artificial Sequence
<220> FEATURE:
<223> OTHER INFORMATION: Oligonucleotide

<400> SEQUENCE: 2
gctgcgctga tagacatcca tg                                           22

THERAPEUTIC VIRAL MICROPARTICLES FOR PROMOTING STENT BIOFUNCTIONALITY AND WOUND HEALING IN VERTEBRATE INDIVIDUALS

CROSS-REFERENCE TO RELATED APPLICATIONS AND DOCUMENTS

This application is a continuation of U.S. patent application Ser. No. 14/783,832, filed Oct. 9, 2015, now U.S. Pat. No. 10,092,607 B2, issued Oct. 9, 2018, which claims the benefit to PCT international Patent Application PCT/CA2014/050369, filed Apr. 11, 2014, which claims priority from U.S. provisional application 61/811,203 filed on Apr. 12, 2013. The content of this priority application is incorporated herewith in its entirety.

SEQUENCE LISTING

This application also contains a sequence listing in electronic, ASCII format. The content of this sequence listing is incorporated herein in its entirety. Said ASCII copy, created on Aug. 20, 2018, is named SEQ.txt and is 819 bytes in size.

TECHNOLOGICAL FIELD

The present disclosure relates to the specific and local delivery of therapeutic nucleic acid molecules to the cells of a vertebrate host for promoting the repair of damaged blood vessels and also for wound healing applications. The therapeutic nucleic acid molecules are provided by polymeric viral microparticles allowing the controlled-release of genetically-engineered baculovirus. The viral microparticles may optionally be formulated in pharmaceutical compositions and/or included in a support for locating at the site of the wound.

BACKGROUND

Percutaneous transvascular coronary angioplasty and stenting is one of the most commonly employed interventional procedures for the treatment of coronary artery disease. A frequent long-term complication of this treatment modality is the phenomenon of in stent restenosis (ISR) which occurs at the site of the atherosclerotic lesion, leading to the obstruction of dilated arteries in 20-30% of patients within 6 months of stenting. The primary contributors of this multifactorial pathological event are incomplete endothelial recovery and vascular SMC proliferation in the inner lining of the artery. Several approaches have been used to improve stent design and durability, such as the use of covered stents to improve biocompatibility of the stent material and intracoronary radiation to inhibit inflammation and proliferation of smooth muscle cells. Radiation therapy, although effective, was accompanied by delayed healing and incomplete endothelial recovery; whereas coated stents have not been completely successful in eliminating the problem.

The introduction of drug eluting stent (DES) has been seen as a significant improvement in the existing stent design. The drugs used are mostly antiproliferative which target the smooth muscle cell proliferation and related inflammatory systems. But the direct use of these chemical factors is limited by the problems associated with drug washout, their inadvertent effects on non-target cells, as well as the unselected inhibition of vascular cell division by the drugs leading to incomplete endothelial recovery of stented vessels. Moreover, recent long term meta-analysis of DES studies demonstrating increased risk of late-stent thrombosis has raised questions on the long term safety of DES. As the pathological recurrence of stenosis mainly stem from the endothelial cell lining damage and dysfunction caused by the stent implantation, approaches to promote accelerated re-endothelialization can be of significant importance to reduce the risk of ISR and late in-stent thrombosis. Moreover, this strategy will evade the harmful consequences of discontinuation of antiplatelet drug therapy which are otherwise needed post DES implantation. Therapeutic induction of vascular cells by transferring proangiogenic vascular genes, such as Vegf, to promote re-endothelization has been proposed as a potent way to attenuate neointima formation and reduce restenosis. Vegf cytokines are a family of endothelial specific mitogenic factors that bind to tyrosine kinase receptors 1 and 2, expressed almost exclusively on the endothelial cells, and widely used for selective proliferation and repair of damaged vascular endothelial structures. Although mammalian viral vectors have been efficiently used for vascular gene therapy, clinical applications are limited due to safety concerns related to risk of inclusion of replication competent viruses and proper optimization of the human tolerization level to these pathogens. Moreover, there are associated problems of immunogenicity due to high viral titer, induction of innate toxicity and inflammatory reactions coupled with the inherent risk of viral integration to the host genome. On the other hand, non-viral gene delivery systems are mainly limited by low in vivo gene transfer efficiencies.

Wound healing is a complex physiological event which leads to the replacement of the injury tissue by a new one. The adequate healing of a wound requires the proliferation and/or dedifferentiation of cells in the vicinity of the wound as well as the production and/or remodeling of the extracellular matrix, but also a return to quiescence once the scar has been formed (differentiation of cells, halt in proliferation and in matrix remodeling). In some pathological instances, the healing process fails or delays the return to quiescence and as such promotes the hyperplasia of cells, the production of an abnormal amount of extracellular matrix (e.g. too much or too little) and can even lead to the formation of a pathological scar (e.g. hypotrophic/hypertrophic scar in the skin, restenosis in large vessels for example).

In situations where the wound healing process is susceptible to induce pathological side-effects (in stent restenosis for example), it is would be desirable to be provided with a gene-delivery system which could favor the homeostatic wound healing process by providing, locally, in the vicinity of a wound, a therapeutic nucleic acid molecule for transduction by the cells of the host. Since the process of wound healing is performed within a specific time window, in some embodiments, it would be highly desirable to be provided with a gene-delivery system which allows a transient transduction of the therapeutic nucleic acid molecule during to the wound healing process. In addition, since a wound is usually limited to a specific location within the host, in some embodiment, it would be highly desirable to be provided with a gene-delivery system which specifically allows the transduction of the therapeutic nucleic acid to the vicinity of the wound.

Preferably, the gene-delivery system limits (and in some embodiments) prevents the immune reaction associated with the transduction of the therapeutic nucleic acid molecule.

BRIEF SUMMARY

The present disclosure provides viral microparticles in which embedded genetically-engineered baculoviruses are used to deliver a therapeutic nucleic acid molecule to the cells of the vertebrate individual. The viral microparticles can be formulated in a pharmaceutical composition and optionally be included in a support. The viral microparticles favor adequate repair of blood vessels as well as wound healing.

According to a first aspect, the present disclosure provides a viral microparticle for the delivery of a recombinant therapeutic nucleic acid molecule to the cells of a vertebrate individual. The viral microparticle comprises, as a first component, a matrix of biocompatible biodegradable polymers. The viral microparticle further comprises, as a second component, at least one (or in an embodiment a plurality of) genetically-engineered baculovirus having a viral genome comprising/encoding the recombinant therapeutic nucleic acid molecule and lacking the ability of replicating in the cells of the vertebrate individual. In an embodiment, the biocompatible biodegradable polymer is/comprises a polyester. In another embodiment, the polyester is/comprises poly(lactic-co-glycolic acid). In still another embodiment, the genetically-engineered baculovirus is from the genera nucleopolyhedrovirus, and in still a further embodiment, the genetically-engineered baculovirus is a multicapsid virus. In yet a further embodiment, the genetically-engineered baculovirus is from the subtype *Autographa californica* multicapsid nucleopolyhedrovirus (AcMNPV). In an embodiment, the genetically-engineered baculovirus is at least partially embedded in the matrix. In another embodiment, the recombinant nucleic acid molecule encodes a growth factor, such as, for example, an angiogenic growth factor (e.g. vascular endothelial growth factor (VEGF)). In another embodiment, the genetically-engineered baculovirus further comprises a coat of cationic polymers covering at least a portion of the surface of the baculovirus. In a further embodiment, the cationic polymers are/comprise dendrimers. In still a further embodiment, the dendrimers are/comprise poly(amidoamine) (PAMAM), such as, for example, a GO PAMAM. In an embodiment, the viral microparticle has a relative diameter between about 5 μm. and about 10 μm.

In a second aspect, the present disclosure provides a process for making a viral microparticle for the delivery of a recombinant therapeutic nucleic acid molecule to the cells of a vertebrate individual. Broadly, the process comprises (a) resuspending, in an aqueous solution, a genetically-modified baculovirus having a viral genome comprising the recombinant therapeutic nucleic acid molecule so as to obtain an aqueous preparation; (b) combining and homogenizing the aqueous preparation of step (a) with a solution of a biodegradable biocompatible polymer and a water immiscible, volatile organic solvent so as to form a water-in-oil (w/o) emulsion; (c) combining and stirring (and optionally homogenizing) the water-in-oil emulsion of step (b) with an oil so as to form a water-in-oil-in-oil (w/o/o) emulsion; and (d) evaporating the water immiscible, volatile organic solvent from the water-in-oil-in-oil emulsion of step (d) so as to form the viral microparticles. In an embodiment, the process further comprises (e) recuperating and washing the viral microparticles obtained in step (d). In an embodiment, the oil further comprises a surfactant, such as, for example, a non-ionic surfactant. In another embodiment, the oil is a vegetable oil. In yet another embodiment, the process further comprises coating, at least partially, the genetically-modified with a cationic polymer prior to step (a).

In a third aspect, the present disclosure provides a viral microparticle for the delivery of a recombinant therapeutic nucleic acid molecule to a vertebrate individual obtained by the process described herein.

In a fourth aspect, the present disclosure provides a pharmaceutical composition having (i) a gelling agent and (ii) the viral described herein or obtained by the process described herein. In an embodiment, the gelling agent comprises a protein and/or a protein fragment, such as, for example, fibrinogen and/or fibrin.

In a fifth aspect, the present disclosure provides a process for formulating the pharmaceutical composition described herein. Broadly, the process comprises combining the gelling agent and the viral microparticle. In an embodiment, the process further comprises cross-linking the gelling agent.

In a sixth aspect, the present disclosure provides a kit for making the pharmaceutical composition described herein. The kit comprises the gelling agent described herein and the viral microparticle described herein In an embodiment, the kit can further comprise a cross-linking agent.

In a seventh aspect, the present disclosure provides a support comprising the viral microparticle described herein or obtained by the process described herein. Alternatively, the support comprises the pharmaceutical composition described herein or made by the process described herein. In an embodiment, the support is solid. In another embodiment, the support is metallic. In still another embodiment, the support is a medical implant, such as, for example a stent.

In an eighth aspect, the present disclosure provides a method of promoting the healing of a wound in a vertebrate individual in need thereof. The method comprising placing a therapeutic effective amount of at least one of: the viral microparticle described herein, the viral microparticle obtained by the process described herein, the pharmaceutical composition described herein, the pharmaceutical composition obtained by the process described herein, or the support described, in the vicinity of the wound so as to favor the healing of the wound in the vertebrate individual. Also contemplated herein the viral microparticle described herein, the viral microparticle obtained by the process described herein, the pharmaceutical composition described herein, the pharmaceutical composition obtained by the process described herein, or the support described herein for promoting the healing of a wound in a vertebrate individual in need thereof as well as the use of the viral microparticle described herein, the viral microparticle obtained by the process described herein, the pharmaceutical composition described herein, the pharmaceutical composition obtained by the process described herein, or the support described herein for promoting the healing of a wound in a vertebrate individual in need thereof

BRIEF DESCRIPTION OF THE DRAWINGS

Having thus generally described the nature of the disclosure, reference will now be made to the accompanying drawings, showing by way of illustration, a preferred embodiment thereof, and in which:

FIGS. 1A-1D provides a schematic representation of design, formulation and mode of action of virus loaded bioactive stent to attenuate ISR. (A) Release of entrapped viruses carrying an exemplary therapeutic nucleic acid molecule encoding angiogenic transgene (Vegf) to the adhering vascular wall. (B) Local overexpression of transgene to enhance endothelial regeneration. (C) Proper cushioning of intima layer with regenerated endothelial monolayer to reduce risk of restenosis by smooth muscle proliferation and thrombosis by avoiding further exposure to blood. With time, the stent loses its coatings due to the biodegradable nature of the polymers, leaving behind the bare stent struts in the already recovered vascular segment. (D) Schematic representation of generation of Bac-PAMAM complex and its subsequent microencapsulation in PLGA microspheres by a w/o/o double emulsion solvent evaporation method.

FIGS. 2A-2E illustrates SEM (A and A') and AFM (B and B') microphotographs of virus loaded PLGA microspheres demonstrating the surface morphology prepared by an embodiment of the method described herein (and illustrated in FIG. 1 D). TEM picture of empty microspheres (C) and virus loaded microspheres (D). (E) represents the ultrathin inner cross-sections of the microspheres loaded with viruses under TEM. Note: The entrapped viruses have a circular shape in the TEM picture because the microphotograph was taken for a single plane on the cut cross-section of the virus loaded microsphere.

FIGS. 3A-3H illustrates the characterization of PLGA MS coated fibrin stent. (A) Uncoated Bare metal stent, (B) Nile red containing MS loaded stent after coating and (C) expanded stent after crimping on a balloon catheter. (D) Fluorescence image of the stent showing the fluorescent PLGA MS embedded on the fibrin stent surface. SEM microphotographs of (E) bare metal stent, (F) fibrin coated stent and (G i and ii) PLGA MS loaded fibrin coated stents. The image in (G ii) is a magnified image of the inset of (G i). (H) Cumulative baculovirus release (in terms of % of initial virus loaded) from stents coated with varying concentrations (50 and 100 mg/ml DCM) of PLGA MS prepared by w/o/w and w/o/o method shows controlled release of virus load over 24 h as a function of the PLGA concentration and MS preparation method. Results are shown as the percentage of active virus cumulative release in function of hours post incubation. Results are shown for MS baculovirus (50) obtained by a water-in-oil-in-oil process (♦) or a water-in-oil-in-water process (■) as well as for MS baculovirus (100) obtained by a water-in-oil-in-oil process (A) or a water-in-oil-in-water process (X).

FIGS. 4A-4D illustrates the surface modification of baculovirus with PAMAM dendrimer (GO). Zeta potential (in mV) (A) and particle size (in nM) (B) of Bac-PAMAM (0) (free Bac), Bac-PAMAM (0.01), Bac-PAMAM (0.1), Bac-PAMAM (0.5), and Bac-PAMAM (1.0), where the values within brackets indicate the ratio of PAMAM molecules in µmol per 108 viruses. The data is represented by mean±standard deviation (SD). TEM images of free Bac (C) and Bac-PAMAM (0.5) (D) suspended in PBS. Arrows indicate the positively charged PAMAM dendrimer coating on the negatively charged baculovirus surfaces to form the hybridized nanostructures. Scale indicates 100 nm length.

FIGS. 5A-5F illustrates the characterization of PLGA-encapsulated Bac. (A) The kinetics of PLGA-encapsulated BacMGFP with or without PAMAM coatings. The prepared stents with encapsulated viral preparations containing 0, 0.01, 0.1, 0.5 and 1.0 µlid PAMAM molecules per 108 baculovirus were incubated in PBS. At the indicated times PBS was collected and used for transduction of HASMCs using standard procedure mentioned in the Example section. Results are shown as the percentage of transduced cells for each type of encapsulated baculovirus 12 h, 18 h or 24 h after transduction. Data represent mean±SD (n=3). (B-E) represents the transduced cells 24 h post transduction under fluorescence field while (B'-E') represents the corresponding bright field. (F) Cytotoxic effect of the above encapsulations on HASMCs after 12 h of incubation was analyzed. Data from different groups were represented in terms of percentage of viable cells in function of the type of encapsulated baculovirus. **=P<0.01 compared to control Bac group (n−3).

Figure 6A:
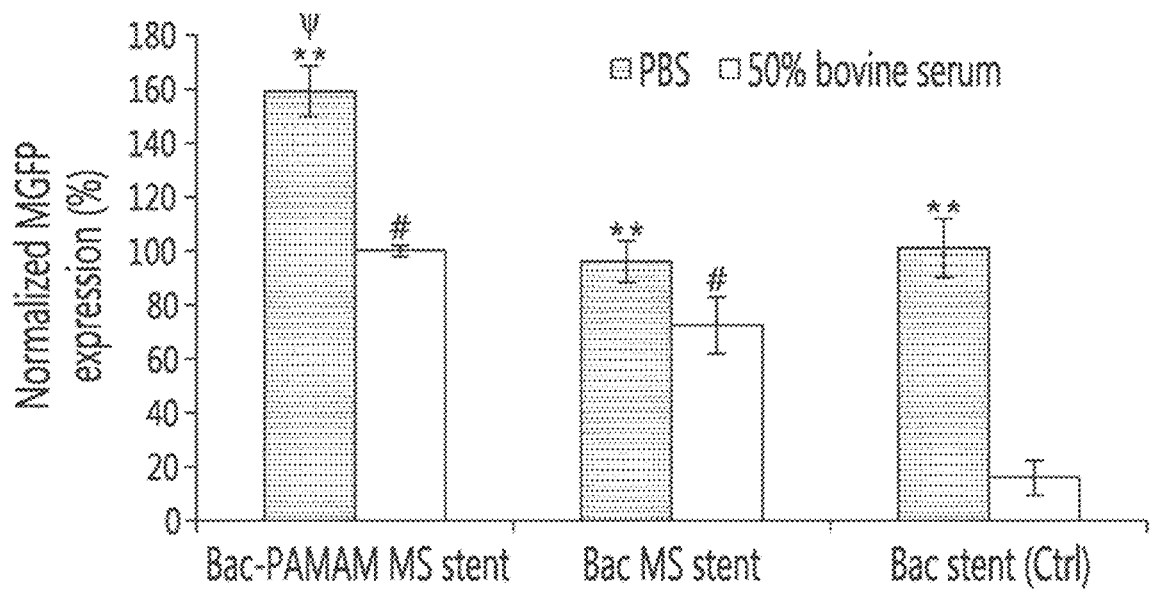
Figure 6B:
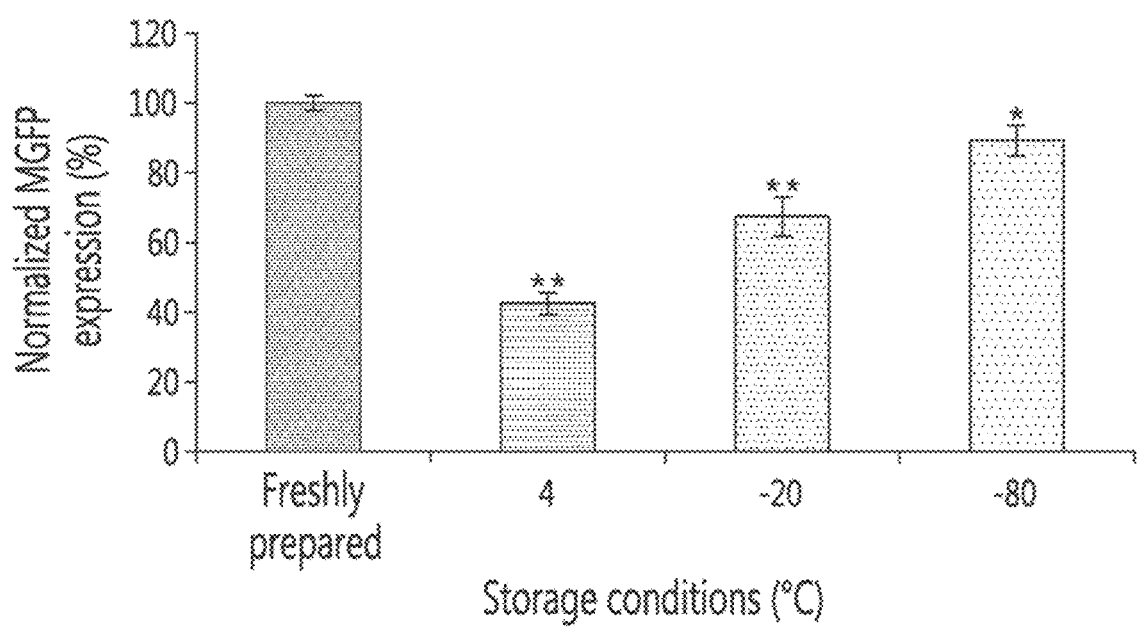

FIGS. 6A-6B illustrates the effect of serum and storage temperatures on bioactivity of BacMGFP loaded stent. The BacMGFP-PAMAM MS, BacMGFP MS and BacMGFP stents, after 1 h incubation in 50% serum or PBS solution, were used to transduce 2×104 HASMCs per well in 96 well-plate using standard method as mentioned in Example I. Similarly, BacMGFP-PAMAM MS stents after storage for 3 months at different temperatures (4° C., −20° C., −80° C. and control freshly prepared) were used to transduce HASMCs in vitro. Data was represented in terms of normalized MGFP expression taking BacMGFP-PAMAM MS expression as 100% (A) and taking freshly prepared stent expression as 100% (B). Data represent mean±SD (n=3). Statistically significant differences within groups are denoted by *=p<0.001 and =P<0.01, while condition-matched differences between groups are represented by ψ<0.001 (PBS) and #<0.001 (serum).

FIGS. 7A-7Dvi illustrates the release and expression of a therapeutic nucleic molecule from the encapsulated baculoviruses. (A) Quantification of VEGF released by transduced HASMCs over time as detected by ELISA. Results are shown as released VEGF (ng/mL) in function of days post-transduction for various types of baculovirus (Bac-PAMAM=♦, Bac only=■ and control=A). (B) Proliferation of HUVECs grown in the presence of conditioned medium (CM from Day 4) from BacVegf-PAMAM (with or without anit-VEGF Ab) and BacVegf transduced HASMCsAs control group, CM from non-transduced cells (Ctrl) was taken. Initial seeding density was 2×104 cells per well in 96 well plate and cell proliferation was detected by a colorimetric assay on day 3. Results are shown for the Day 4 conditioned medium obtained from different types of baculovirus (Control, Bac Vegf only, BacVegf-PAMAM (0.5) and Bac Vegf-PAMAM with anti-VEGF antibodies). ANOVA: Significantly higher values in groups compared to control are denoted by *=P<0.001 and =P<0.01. (C) Induction of HUVEC migration in an in vitro wound healing assay. Results are shown as the percentage of would healing in function of different types of encapsulated baculoviruses or control (control, Bac Vegf only, Bac Vegf-PAMAM or Bac Vefg-PAMAM with anti-VEGF antibodes). HUVEC cell monolayer was wounded with cell scraper and treated with CM from above mentioned groups. HUVEC were photographed (200×) after 24 h treatment and percentage of scratched area (marked by the white dotted border line) covered by the migrated cells were analyzed using Image J software (C i=representative image of the control, ii=representative image of Bac Vegf only, iii=representative image of Bac Vegf-PAMAM and iv=representative image of Bac Vegf-PAMAM and anti-VEGF antibodies). (D) Effect of CM from above mentioned groups on tubular formation in vitro. After 18 h co-cultivation with HUVECs, tubular formation was evaluated. The graphs represent the relative tubule length in µli taking BacVegf as 100% (D i) and counting of capillary tubule number (D ii). The data represent the mean±SD of three independent experiments. (D iii-vi) Properly formed tubular structure was observed in BacVegf-PAM AM (v) and BacVegf (iv) groups, compared to the unstimulated control (iii) and Ab treated (vi) group as examined using a fluorescent microscope under 100× magnification.

FIGS. 8Ai-8Civ illustrates the experimental procedure and results for the in vivo experiment in a canine model. The femoral artery was first isolated from the normal blood flow using clips (A i). The selected portion was then flushed with PBS followed by severe balloon injury using balloon catheter (A ii). This was followed by the insertion of the crimped polymer coated stent in the damaged artery. The balloon catheter carrying the stent was inflated to implant the stent at the site. This was followed by deflation and removal of the balloon catheter (A iii). (B) hVegf transgene delivery and expression in the artery. RT-PCR of tissue retrieved from stented vessel segments was performed to identify the hVegf gene, detecting PCR product. Two (2) weeks post stent implantation in Coated (+) group, the VEGF transcript was still present in the proximal (P), middle (M) and distal (D) portions of the stented artery. But transcript was undetectable in the artery sections 1 cm proximal (P') and distal (D') to the stented portion as well as in the Coated (−) control group on both week 2 and week 16. Importantly, the transcript also disappeared in Coated (+) group by week 16 confirming the transgene nature of expression of the viral system. (C) Immunohistochemical localization of VEGF within stented femoral artery in Coated (+) group at week 2 post stent deployment in the proximal (i), middle (ii) and distal (iii) portions of the stented artery as well as in a control artery (iv). Coated (−) was taken as control. The VEGF expression was noticed mainly in the intima and outer medial layer. Note that the expression occurred mainly at the strut area (white dotted) where the stent surface touched the inner lining of the artery, with no significant expression in the neointimal area indicating that the gene transfer from stent surface occurred only at the very early stage of deployment.

FIGS. 9Ai-9D illustrates the re-endothelialization of vessels following stent implantation. (A) Evans blue staining confirms that Coated (+) group (i) was able to recover the injury by endothelialization while in Coated (−) group (ii) the wounds was still exposed with high amount of Evans blue uptake. Control artery segment with no injury showed no signs of dye uptake (iii). (B) Quantification of percentage re-endothelialization week 2 after staining using imaging software in the Coated (+) and Coated (−) group. The data represent the mean±SD (n=3). (C) SEM pictures of Coated (−) stent on week 2 (C i) and week 16 (C ii) and that of Coated (+) stents on week 2 (C iii) and week 16 (C iv). Vessels from Coated (−) group lacked endothelial cell morphology between struts, while endothelial cell monolayer completely covered the stent surface with typical fusiform morphology and intact borders in Coated (+) group. (D) Histological assessment of re-endothelialization of arterial tissue sections (measured as the percentage of re-endothelialization at week 16 after deployment) in Uncoated, Coated (−) and Coated (+) at week 16 post stent deployment. The data represent the mean±SD (n=8). ANOVA: ***=P<0.001 and *=P<0.05, while P value on comparing Coated (+) and Coated (−) in (D) is denoted by ψ).

FIGS. 10A-10D illustrates the effect of BacVegf-PAMAM delivery on ISR assessed by angiography analysis. Comparison of angiography studies at week 16 after stent deployment in femoral arteries of dogs. Representative angiographic images of femoral arteries with uncoated bare metal stent (A') and stents coated carrying BacNull-PAMAM (B') and BacVegf-PAMAM (C) at week 16 after stent deployment, where (A), (B) and (C) shows the corresponding stent positions before angiography (black arrows).

Image analysis within the proximal (dotted white arrows) and distal (white arrows) regions of stented arteries (dotted line) demonstrated significantly reduced ISR in Coated (+) group compared to Uncoated group, although significance was not achieved when compared to Coated(−) (D). Results are shown as the percentage of stenosis area as determined by angiography in function of the different treatment. The data represent the mean±SD (n=8). ANOVA: ***=P<0.001. P value on comparing Coated (+) and Coated (−) is denoted by ψ).

FIGS. 11Ai-11F Cross-sectional view of stented artery through SEM demonstrating the intimal hyperplasia over the protruded stent struts. (B) The effect of BacVegf-PAMAM delivery on ISR assessed by histomorphometric analysis. Comparison of histomorphometric studies at week 16 after stent deployment in dog femoral arteries. Representative cross-sectional images of elastic Van Gieson stained femoral arteries with uncoated bare metal stent (B i-iii) and stents coated carrying BacNull-PAMAM (C i-iii) and BacVegf-PAMAM (D i-iii) at week 16 after stent deployment. Percentage stenosis (E) and mean neointimal area (F) analysis at the stented regions demonstrated significantly reduced ISR in Coated (+) group compared to Uncoated and Coated (−) groups. The data represent the mean±SD (n=8). ANOVA: **=P<0.01; P value on comparing Coated (+) and Coated (−) is denoted by ψ).

DETAILED DESCRIPTION

In accordance with the present disclosure, there is provided a viral microparticle for promoting wound healing in a vertebrate individual. The viral microparticle is made up of a polymeric matrix in which genetically-engineered baculoviruses are at least partially embedded. The viral microparticles are to be located in the vicinity of a wound and are designed to locally discharge or elute, in a controlled fashion, the embedded genetically-engineered baculoviruses. The genetically-engineered baculovirus serve as a delivery system to introduce a therapeutic nucleic acid molecule into the cells in the vicinity of the wound and allow for the transduction of the therapeutic nucleic acid molecule by the cellular machinery of the infected cells. In order to locate the viral microparticles in the vicinity of a wound, it is possible to formulate them as pharmaceutical formulations and even include them onto a support (such as a stent for example). The present disclosure also provides methods of using the viral microparticles to promote wound healing in a vertebrate individual.

In embodiments of the present disclosure in which the therapeutic nucleic acid molecule is intended to favor the healing of a wound caused by the insertion of a stent in a large vessel, an approach where invertebrate originated insect cell specific recombinant baculovirus can be used to locally deliver a therapeutic nucleic acid molecule (e.g. a VEGF transgene), thereby promoting the endothelialization of the stent and preventing ISR. Baculovirus offers a unique advantage over other delivery systems because of its ability to efficiently transduce non-dividing cells, inherent inability to replicate in mammalian cells, low cytotoxicity even at high viral dosage, absence of preexisting antibodies against baculovirus in animals and ease of production scale up to high titers. To protect the baculovirus from serum inactivation and achieve a controlled release at the target site, the baculovirus is embedded (at least partially) within polymeric-based microparticles. In some optional embodiments, it may also be beneficial to enhance the gene transduction efficiency by surface-functionalizing the baculovirus with cationic polymer (such as, for example a synthetic PAMAM dendrimer). Further, in alternative embodiments, to locate the viral microparticles on the stent, a coat of multi-layered fibrin can be used.

Without wishing to be bound to theory, it is postulated that, in an embodiment of the present disclosure, e.g. a therapeutic gene eluting stent formulation, can efficiently deliver angiogenic vascular genes to the affected site and induce favorable therapeutic effect in the local vascular biology as illustrated in FIG. 1. FIG. 1A shows the initial stage of wound repair by the coated stent, an embodiment of the present disclosure. A stent 071 comprising PLGA microspheres 060 with entrapped dendrimer-coated and genetically-engineered baculoviruses 020 is placed a location 070. At location 070, the endothelium that has been damaged (for example by the placement of the stent 071). Location 070 comprises a smooth muscle cell layer 010 (also referred to as a media) and injured endothelial cell monolayer 030 (also referred to as an intima). In the embodiment described on FIG. 1A, the stent comprises a fibrin layer 050 comprising viral microspheres 060. Viral microspheres 060 are either outside or inside from the fibrin layer 050 and can release the genetically-engineered viruses 020 in the vicinity of location 070. FIG. 1 B shows the transduction of the virally-delivered therapeutic nucleic acid molecule by cells located in the vicinity of the wound/stent location. Cells 080 transduced by the genetically-engineered viruses 020 of FIG. 1A overexpress the therapeutic protein/growth factor 090 encoded by the transgenic therapeutic nucleic acid molecule (e.g., in the present embodiment, VEGF). Meanwhile, the stent 071 can contain empty microspheres 100. FIG. 1 C illustrates the end of the wound healing process. At location 110, which was previously wounded, an healed inner lining of artery can be observed. The re-endothelialization of the previously denuded endothelial layer 120 is now complete by the presence of newly generated endothelial cells 120. The fibrin layer 050 (comprising empty or complete PLGA microspheres) of the stent 071 can continue its biodegradation.

Viral Microparticles

The present disclosure provides viral microparticles for the local delivery of a therapeutic nucleic acid molecule. In order to mediate their therapeutic effects, the therapeutic nucleic acid molecules need to enter (e.g. be delivered to) the cells of the treated individual and be transcribed/translated by the cellular machinery of the cells of the treated individual. The viral microparticles described herein are especially well suited to favor ordered wound healing and/or limit (or in some embodiments even prevent) pathological wound healing (such as for example hyperplasia of cells involved in the healing of the wound) and/or for the healing of large blood vessels. The viral microparticles can be used in a wide variety of vertebrate hosts, providing that the cells of the treated host do not allow the replication of the recombinantly-engineered baculovirus. As such below, the viral microparticles described herein are especially useful for the treatment of wound in vertebrate individuals and, in some embodiments, in mammals (such as humans, dogs, horses, etc.).

The viral microparticles of the present disclosure are not limited to a particular genera, type or subtype of baculovirus. Baculoviruses are a large family of rod-shape viruses which have a circular double-stranded DNA-based genome. Baculoviruses have very species-specific tropisms among the invertebrates. Even though baculoviruses are capable of entering (e.g. infecting or transducing) mammalian cells in culture they are not known to be capable of replication in mammalian or other vertebrate animal cells. Further, the baculovirus genome is not know to integrate in the genome of a vertebrate host cell and is ultimately degraded by the host cell within a couple of days, thereby limiting the presence of the virus in the infected vertebrate host.

The baculovirus that can be included in the viral microparticles described herein is can be from the granuloviruses (GV) genera. Such baculovirus usually contain a single capsid per viral envelop and is usually occluded in a granulin matrix. In an alternate embodiment, the baculovirus which can be included in viral microparticle can be from the nucleopolyhedrovirus (NPV) genera. Baculovirus of the NPV genera contain either single (SNPV) or multiple (MNPV) nucleocapsids per envelope and are usually occluded in a polyhedrin matrix. As show below, the subtype *Autographa californica* multicapsid nucleopolyhedrovirus (AcMNPV) was successfully used in exemplary embodiments of the viral microparticles described herein. Baculovirus of the AcMNPV subtype are extensively used and characterized by those skilled in the art. However, the viral microparticle of the present disclosure can also comprises other baculovirus subtypes, such as, for example *Bombyx mori* nucleopolyhedrovirus (BmNPV).

The viral microparticles comprises a recombinantly-engineered baculovirus embedded in a polymeric matrix. The baculovirus' genome serves as a vector for delivering the therapeutic nucleic acid molecules to the cells of the treated individuals. In the gene-delivery system described herein, the baculovirus is used because of its intrinsic ability to enter into the cells (e.g. infect/transduce the cells) of the vicinity of the wound (even though the cells may not be under active division, e.g. resting/non-dividing cells) and have the therapeutic nucleic acid molecule transduced by the cellular machinery of the infected cells. The baculovirus is labeled "genetically-engineered" because it has been manipulated to include, within its viral genome, an heterologous therapeutic nucleic acid molecule. More specifically, the therapeutic nucleic acid molecule has been integrated (and in an embodiment, specifically integrated), into the baculovirus genome. In an embodiment, the therapeutic nucleic acid molecule can be specifically integrated in the baculovirus' genome, for example, downstream of the polyhedrin gene. As used in the context of the present disclosure, the therapeutic nucleic acid molecule is considered "heterologous" to the baculovirus because it is not natively found in the viral genome. As also used in the context of this disclosure, the term "therapeutic", when used in conjunction with the expression "nucleic acid molecule" refers to the ability of the nucleic acid molecule to provide therapeutic benefits to the infected host and not to the baculovirus itself. In an embodiment, the transgenic/heterologous nucleic acid molecule is derived from the species of the vertebrate host intended to receive the transgenic/heterologous nucleic acid molecule.

In some embodiments, the therapeutic nucleic acid molecule is integrated into the baculovirus' genome while maintaining an operative linkage (and in some embodiments a direct operative linkage) with a promoter which is going to be recognized and used by the cellular machinery of the intended infected/transduced host cell to allow (or increase) the expression of the therapeutic nucleic acid molecule. The present disclosure is not limited to any particular promoter from any particular origin as long as the promoter is recognized and used by the cellular machinery of the infected/transduced host cells. Promoters endogenous as well as heterologous to the baculovirus can be successfully used. Constitutive as well as regulated promoters can be used, depending on the intended therapeutic use. However, as shown below, a constitutive viral promoter (for example a viral promoter from cytomegalovirus) has been successfully used to allow/increase the expression of the therapeutic nucleic acid molecule in the infected/transduced vertebrate cell.

The heterologous therapeutic nucleic acid molecule integrated into the baculovirus genome can encode, for example, a mammalian protein, such as VEGF. The nucleic acid molecule is considered heterologous to the baculovirus because it encodes a protein which is not natively found or expressed by the virus. The nucleic acid molecule is also considered therapeutic to the infected/transduced host because it provides a therapeutic benefit, such as, for example, rapid endothelialization of a stent and thereby reduces the risk of ISR in the treated host (when compared to an untreated host).

This gene-delivery system is not limited to any particular nucleic acid molecule (or encoded protein). As show herein, the therapeutic nucleic acid molecule can be used to increase the expression of a protein (or a plurality of proteins) to provide a therapeutic benefit and, in some embodiments, favor wound healing. In an embodiment, the heterologous therapeutic nucleic acid molecule encodes a protein, such as a growth factor, which will be useful for promoting wound healing. In some embodiments, especially when a blood vessel is injured or ruptured in the wound, the growth factor can be an angiogenic growth factor. A growth factor is considered angiogenic when it has to ability to promote the formation and establishment of a blood vessel. For example, angiogenic growth factors can promote endothelial cell proliferation, migration, extracellular matrix remodeling, endothelial cell tube formation and stability (e.g. association with smooth muscle cells and/or pericytes). Such growth factors include, but are not limited to, vascular endothelial growth factor (VEGF, including VEGF-A, PGF, VEGF-B, VEGF-C and VEGF-D), fibroblast growth factor (FGF, including FGF-1 and FGF-2) as well as angiopoietin (Ang including Ang1, Ang2, Ang3 and Ang4).

However, in another embodiment, the therapeutic nucleic acid molecule does not need to encode a protein and can be used as a source nucleic acid transcripts (miRNA, siRNA, triplex oligonucleotides, ribozymes, etc.) which will modulate (e.g. increase or decrease) the transcription of specific genes in infected cells to mediate their therapeutic effects and ultimately promote wound healing.

Since the baculovirus is used to mediate the transfer of the therapeutic nucleic acid molecule to cells in the vicinity of a wound, the virus must be able to enter or infect the cells in the vicinity of the wound. Such cells include, but are not limited to, mesenchymal cells (such as fibroblasts, adipocytes, pre-adipocytes), stem cells (mesenchymal or other), vascular tissue cells such as endothelial and muscle cells (such as smooth muscles cells or pericytes).

Optionally, the surface of the baculovirus that is included in the viral microparticle can be functionalized to increase cell penetration, increase nuclear localization and/or provide location specificity. Such surface functionalization can be made by covalently attaching to the surface of the baculovirus peptides which are known to increase cell penetration, increase nuclear localization and/or provide cell specificity. Alternatively, the baculovirus can be genetically engineered to express, on its surface, peptides which are known to increase cell penetration, increase nuclear localization and/ or provide cell specificity. Such peptides include, but are not limited to, cell-penetrating peptides such as TAT peptide (a transcriptional activator protein encoded by human immunodeficiency virus type 1 (HIV-1)), bioactive ligands such as the RGD peptide as well as synthetic polymers such as polyethylenimine (PEI) and poly-L-lysine (PLL). Alternatively, the peptide can also be used to localize the baculovirus to a specific location, for example the extracellular matrix.

Optionally, the baculovirus that is included in the viral microparticle is coated with a cationic polymer prior to its incorporation in the viral microparticle. As it is know in the art, baculoviruses have a relatively negatively charged surface which may interfere (e.g. limit) gene delivery/transduction efficiency. As such, but providing a cationic "coat" to the baculovirus surface, it may be possible, in some embodiments, to increase gene delivery/transduction efficiency. The cationic polymer that can be used to coat the baculovirus does not need to be covalently associated to the surface of the baculovirus, it can be non-covalently associated to the surface of the baculovirus by electrostatic/ionic interactions. The cationic polymer can be used to substantially completely coat the surface of the baculovirus or at least coat the majority of the surface of the baculovirus' envelope. In some embodiments, the cationic polymeric coat can be used to enhance the protection the baculovirus against degradation that may occur once it is introduced into a vertebrate host (for example, from serum).

The cationic polymer can be a linear, a branched and/or a circular polymer. In some instances, it is beneficial to use a single type of cationic polymer to form the coat. However, in other embodiments, it may be necessary to use more than one type of polymers. In additional embodiments, it is preferred that the polymer possesses at least one (and even more preferably a plurality) available amino group(s) to provide cationic character. Alternatively, other groups other than amino can be present to provide cationic character. The cationic polymer is also preferably considered soluble in water. In yet another embodiment, once coated with the cationic polymer, the viral particle has a net positive zeta potential when measured at a physiological pH (e.g. between 7.0 and 7.6, usually between 7.3 and 7.4).

Even though the cationic polymeric coat is not limited to any particular cationic polymer, as shown below, a cationic dendrimer can be used to form the baculovirus coat. As known in the art, dendrimers are repetitively branched molecules. A dendrimer is typically symmetric around the core, and often adopts a spherical three-dimensional morphology. In the Examples provided herein, a G-0 poly (amidoamine) dendrimer (or PAMAM) has been successfully used to coat the baculovirus' surface (e.g. envelop). The core of PAMAM is a diamine (commonly ethylenediamine), which is reacted with methyl acrylate, and then another ethylenediamine to make the generation-0 (G-0) PAMAM. Successive reactions create higher generations, which tend to have different properties. Other dendrimers can be used in combination of PAMAM or to replace PAMAM.

Additional cationic polymers include polypeptide-based polymers, such as homo-polypeptides. One homo-polypeptide of interest is poly-L-lysine (or E-Polylysine). Poly-L-lysine is typically produced as a homo-polypeptide of approximately 25-30 L-lysine residues. In contrast to the conventional peptide bond that is linked by the alpha-carbon group, the lysine amino acids of poly-L-lysine are molecularly linked by the epsilon amino group and the carboxyl group.

In some embodiment, polybrene can be used as a cationic polymer. Polybrene (1,5-dimethyl-1,5-diazaundecamethylene polymethobromide, hexadimethrine bromide) is known to be a cationic polymer used to increase the efficiency of viral infection of certain cells. It is believed that polybrene acts by neutralizing the charge repulsion between virions and sialic acid on the cell surface.

Another cationic polymer that can be used to coat the baculovirus is polyethyleneimine (or PEI). PEI is a polymer with repeating unit composed of the amine group and two carbon aliphatic CH2CH2 spacer. PEI can be provided in a linear form (containing all secondary amines), in branched form (containing primary, secondary and tertiary amino groups) as well as in dendrimeric form.

The "naked" (e.g. not coated with the cationic polymer) or "coated" (e.g. coated with the cationic polymer) baculoviruses are not introduced into a host directly in the wound or at the vicinity of a wound. In the context of the present disclosure, they are embedded in a polymeric matrix to form a viral microparticle prior of being introduced into the host. The polymeric matrix is used to release, in a controlled fashion, the baculovirus in the wound or in the vicinity of the wound. Baculoviruses formulated in such polymeric devices are released either by diffusion through the polymer barrier, or by erosion of the polymer material, or by a combination of both diffusion and erosion mechanisms. As used in the context of the present disclosure, the expression "controlled release" refers to the discharge of baculovirus in response to stimuli and/or time. The polymeric matrix thus prolongs therapeutic benefits but also attempts to maintain the delivery of therapeutic nucleic acid molecule within the therapeutic window to avoid potentially hazardous peaks in baculovirus concentration/transgene expression following administration.

In addition, although the term viral "microparticles" is used throughout the present text, it is not limited to a particular shape or size of particles. It encompasses particles which are considered microspheres, microcapsules, nanocapsules as well as nanospheres. The relative size of the viral microparticles can be in the micromolar range. In an embodiment, the relative size of the microparticle is at least 5 µm, 6 µm, 7 µm, 8 µm or 9 µm and/or at most 10 µm, 9 µm, 8 µm, 7 µm or 6 µm as well as any combinations therefrom (for example from 5 µm to 10 µm). In the embodiment in which the viral microparticles are of a relatively spherical shape, the relative diameter of the microparticle is at least 5 µm, 6 µm, 7 µm, 8 µm or 9 µm and/or at most 10 µm, 9 µm, 8 µm, 7 µm or 6 µm as well as any combinations therefrom (for example from 5 µm to 10 µm).

Consequently, because the polymeric matrix of the microparticle needs to be degraded to allow the discharge of the genetically-engineered baculovirus, it has to be biodegradable (e.g. have the intrinsic ability to be cleaved/destroyed within the host). In an embodiment, the polymeric matrix is capable of being degraded/eroded by water. Further, because the polymeric matrix needs to be introduced into a host, it also has to be biocompatible (e.g. have the ability to perform its desired function without eliciting any undesirable local or systemic effects in the host, such as, for example, immune rejection or inflammation). Since the polymeric matrix is going to be used to embed the genetically-modified baculovirus, it should preferably be made from a polymeric material which has the ability to form a matrix under conditions which will not interfere with the infectivity/integrity of the baculovirus. Depending on the required biodegradability of the viral microparticle, the matrix of the viral microparticle can be made from a single type of polymer or more than one of polymers. Further, in some embodiment, and depending on the type of polymeric material used, the polymer of the matrix can be cross-linked to increase the stability/rigidity of the viral microparticle.

Even though the matrix of the viral microparticle is not limited to any particular type of polymer, as shown below in the Examples section, polyesters can be success used to produce such matrix. The polyesters that can be used can be, for example, of synthetic nature and have, in yet another embodiment, an aliphatic main chain. In the Examples below, poly(lactic-co-glycolic acid) (also referred as PLGA) has been used to form the matrix of the viral microparticle. PLGA is a polyester which can be conveniently degraded through the hydrolysis of its ester linkages in the presence of water.

However, in the context of the present disclosure, it is also contemplated that other biodegradable polyesters can be used, alone or in combination with PLGA). Such alternatives polyesters include, but are not limited to polycaprolactone (or PCL), poly (glycerol sebacate) (PGS) and polylactide (or PLL).

As indicated herein, the baculoviruses are embedded within the polymeric matrix. The baculovirus are embedded at least partially (and in some embodiments entirely) within the matrix. It is assumed that the type of baculovirus embedment will vary depending on the nature of polymeric matrix as well as on the process for making the viral microparticles. In some embodiments, the baculovirus is completely embedded in the polymeric matrix such that the external elements of the baculovirus' envelop are in direct contact with the polymeric matrix. In complementary or alternative embodiments, the baculovirus is partially embedded in the polymeric matrix such that a portion of the external surface of the baculovirus' envelop is located inside the polymeric matrix and another portion of the external surface of the baculovirus' envelop is protruding away the polymeric matrix. It is contemplated that some viral microparticles will comprises only completely embedded baculovirus, other viral microparticles will comprise only partially embedded baculovirus whereas other viral microparticles will comprise both completely and partially embedded baculovriuses.

As indicated above, the size and shape of the microparticle will depend on the properties of the polymeric material to make the matrix as well as the process used for making the viral microparticles. In some embodiments, the viral microparticles will have a relatively spherical shape (even though embedded baculovirus may protrude from the surface of the microparticle). In other embodiments, the viral microparticles have a relative diameter of at least 5 µm. In another embodiment, the viral microparticles have a relative diameter of around 10 µm, depending on the solvents used for the preparation such as water/oil/water emulsion method or water/oil/oil emulsion, as well as based on the method such as homogenization or sonication.

The viral microparticles can be directly introduced into a wound or in the vicinity of a wound to mediate their therapeutic effect. The viral microparticles can be physically located to a wound or its vicinity via deposition or injection for example.

Process for Making Viral Microparticles

Depending on the type of polymeric material used to form the viral microparticle's matrix, various processes can be used to make the viral microparticle. However, as shown below, it is beneficial, in some embodiment, to make the viral microparticles as a water-in-oil-in-oil emulsion to preserve the integrity/limit the damage of the embedded baculovirus.

An embodiment for making the viral microparticles is shown in FIG. 1 D. In a first (optional) step, the genetically-engineered baculoviruses 140 can be admixed with a cationic polymer 150 (such as, for example, GO-PAMAM dendrimer) to form a complex 160. The complex 160 is made up of genetically-engineered baculoviruses 140 and the cationic polymer 150 exhibiting ionic interactions with one another. The surface charge of the complex 160 is less negative than the surface charge of the "naked" baculovirus 140. In a second step, the genetically-engineered baculoviruses 140 (not shown) or the complexes 160 (shown on this figure) are introduced into an aqueous solution to form an aqueous phase 170. In some embodiments, this aqueous solution can be an aqueous saline (for example a phosphate-buffered saline) optionally comprising isotonic and/stabilizing agents such as glycerol and/bovine serum albumin. A first oil phase 180 is also provided by combining polymerizable biodegradable and biocompatible polymers (e.g., PLGA in this embodiment) in a water immiscible and volatile organic solvent (e.g., dichloromethane in this embodiment) which can optionally contain a surfactant (e.g. acetonitrile in this embodiment). A water-in-oil (w/o) emulsion is prepared by combining the water phase 170 and the oil phase 180 in an homogenizer 190. The water phase 170 and the oil phase 180 are homogenized until a water-in-oil emulsion 200 is formed. In the water-in-oil emulsion 200, the genetically-engineered baculoviruses are located in the water phase of the emulsion. A water-in-oil-in-oil emulsion is then prepared by combining the water-in-oil emulsion 200 with a second oil phase (not shown, containing a biocompatible oil (for example a vegetable oil e.g., corn oil) and a surfactant (Span 80)) and stirring or homogenizing the resulting mixture 210 with an homogenizer 190. The water-in-oil emulsion 200 and the second oil phase are submitted to homogenization until a water-in-oil-in-oil 220 emulsion is formed. The baculoviruses are located in the water phase of the water-in-oil-in-oil 220 emulsion. The water-in-oil-in-oil emulsion 220 can be then left to stand allow the hardening of the viral microspheres and the evaporation of the water immiscible and volatile organic solvent of the resulting mixture 230. Optionally, the viral microspheres 240 can be centrifuged washed and collected.

One of the processes for making the viral microparticles described herein first comprises resuspending, in an aqueous solution, the genetically-engineered baculovirus. The aqueous solution can comprise elements which help maintaining the integrity of the viral particles, such as for example an isotonic and buffered solution (e.g. a phosphate buffered saline containing glycerol and/or a stabilizing agent (for example bovine serum albumin)). As indicated above, the baculovirus can be "naked", "coated" with a cationic polymer and/or "surface-functionalized" prior to its resuspension in the aqueous solution.

The resulting aqueous preparation (e.g. resuspended baculovirus) is then combined with a solution of the biodegradable biocompatible polymer (which will eventually form the matrix of the viral microparticle) and mixed to obtain a water-in-oil (w/o) emulsion. The biodegradable biocompatible polymer can be polymerizable to form a polymeric matrix. To favor the emulsion, in an embodiment, a surfactant (such as for example acetonitrile, polyvinyl alcohol) (PVA) and/or polyvinyl pyrrolidone) (PVP)) can be used. The surfactant is preferably added to the oil phase prior to the emulsion. Due to the chemical nature of the biodegradable biocompatible polymer, it is necessary to solubilize it in a water immiscible, volatile organic solvent to provide a single phase prior to combining it to the resuspended baculovirus aqueous preparation. For example, when PLGA is used as the biodegradable biocompatible polymer, a wide variety of water immiscible, volatile organic solvents can be used. Such solvents include, but are not limited to chlorinated solvents (such as, for example dichloromethane (DMC)), tetrahydrofuran, acetone or ethyl acetate In addition, even though various techniques are known to those skilled in the art to achieve the w/o emulsion, in order to preserve the integrity/infectivity of the baculovirus, it may be beneficial to use an homogenization method instead of more disruptive ones (sonication for example).

Once the water-in-oil emulsion is formed, it is combined and mixed with an oil to form a water-in-oil-in-oil (w/o/o) emulsion. For this second emulsion, any type of biocompatible oil can be used (e.g. vegetable oil such as corn oil for example). In some embodiment, the oil can be supplemented with a biocompatible non-ionic surfactant (e.g. Span 80™ for example) prior to the second emulsion. Even though various techniques are known to those skilled in the art to achieve the w/o/o emulsion, in order to preserve the integrity/infectivity of the baculovirus, it may be beneficial to use an homogenization technique instead of more disruptive ones (sonication for example).

Once the w/o/o is achieved, the solution can be stirred under conditions to allow the evaporation of the water immiscible, volatile organic solvent and, ultimately, the formation of the hardened viral microparticles. In embodiments, it may be necessary to recuperate the viral microparticles and wash them to remove additional impurities (such as, for example, unembedded baculovirus).

The process described herein can be completed at ambient temperature.

Pharmaceutical Compositions of Viral Microparticles

Even though the viral microparticles can be used on their own and placed directly within a wound or in the close vicinity of a wound, in some embodiment, it can be beneficial to provide the viral microparticles in the form of a pharmaceutical composition. Besides comprising the viral microparticles described herein (or produced by the process described herein), the pharmaceutical composition also comprises a component capable of forming a matrix in which the viral microparticles are dispersed. Depending on the intended use, the viral microparticles can be relatively homogeneously or heterogeneously dispersed within the matrix of the pharmaceutical composition. The matrix can also serve to control the release of the viral microparticles at the vicinity of a wound.

In one embodiment, the pharmaceutical comprises a gelling agent as a component capable of forming a matrix. The gelling agent is capable of forming a gel (e.g. a cross-linked system which exhibits no flow when in the steady-state) in which the viral microparticles are dispersed. In the pharmaceutical composition, the gelling agent can be in a liquid or a solid form. However, once introduced into the vicinity of a wound (for example in a cavity formed by the wound), the gelling agent is preferably in a solid form to limit displacement of the pharmaceutical composition away from the wound, and ultimately allow the local delivery of the baculovirus. The gelling agent is intended to be biocompatible with the treated vertebrate individual as well as being capable of preserving the integrity of the viral microparticles.

In some advantageous embodiments, the gelling agent is capable of forming a hydrogel (a gel comprising water molecule(s)). In additional embodiments, the gelling agent can comprise a cross-linkable protein, and in even a further embodiment, a cross-linkable protein derived from a clot (fibrinogen for example) and/or the extracellular matrix (collagen, laminin, elastin, fibronectin for example). In alternative embodiments, the gelling agent can be a nonproteinaceous element (or combination thereof) of the extracellular matrix (glucoasminoglycan (heparan sulfate, chondroitin sulfate, keratan sulfate), hyaluronic acid for example). In further embodiments, the gelling agent can be a synthetic nanomaterial such as, for example, a polymeric nanoscaffold and/or a nanoporous material. The gelling agent can also comprise more than one type of gellable entity. The type of gelling agent that can be included in the pharmaceutical composition is not limited to the exemplary embodiments described herein. For example, the gelling agent may also include be collagen, gelatin, extracellular matrix based hydrogels, covalently or ionically conjugated hydrogels, composite or hybrid hydrogel structures, photocrosslinkbale hydrogels as well as combinations thereof.

As indicated above, the pharmaceutical composition can be provided in a liquid form. In such embodiment, it will be necessary to convert the pharmaceutical composition into a solid form either prior to administering it to the vertebrate individual or upon administration to the vertebrate individuals. In embodiments in which the gelling agent needs to be cross-linked with a cross-linking agent (for example fibrinogen and its associated cross-linking agent thrombin), the pharmaceutical composition can be provided as a kit comprising the gelling agent (optionally already comprising the viral microparticles) and the cross-linking agent.

In embodiments in which the gelling agent needs to be heated to allow the formation of a solid composition, the pharmaceutical composition (optionally already comprising the viral microparticles) can be provided with instructions on the conditions to be used to achieve a solid form.

As also indicated above, the pharmaceutical composition can also be provided in a solid form which is ready to be administered to the vertebrate individual in need thereof. In such embodiment, the pharmaceutical composition preferably already comprises the viral microparticles dispersed therein.

In order to formulate the pharmaceutical compositions described herein, it is possible to combine the gelling agent and the viral microparticles. In an embodiment, the gelling agent is in a liquid form when it is first admixed with the viral microparticles and then transformed into a gel (which can optionally include a step of adding a cross-linking agent to the mixture and/or submitting the mixture to a heat treatment).

Viral Microparticles Comprising Supports

In order to administer the viral microparticles described herein, it is possible to add/include them to a biocompatible support and introduce such support in the wound or its vicinity. Alternatively, it is also possible to apply the pharmaceutical composition onto or within the support. When the pharmaceutical is provided in a solid form, it is possible to attach it on the support by mechanical means (a suture or a clip for example) or add a linker to increase the adhesiveness of the pharmaceutical composition to the solid support (e.g. fibrin glue for example). When the pharmaceutical composition is provided in a liquid form, it is possible to apply it on a support (e.g. coating, dipping, rolling, brushing, etc.) and cause the pharmaceutical composition to gel on the surface of the support. One exemplary embodiment of such process included the coating of the support with a fibrinogen mixture comprising the viral microparticles and the subsequent coating of the support with a thrombin solution which causes the formation of a fibrin gel (comprising the viral microparticles) on the support.

In the context of the present disclosure, it is not necessary to coat entirely the support to observe a beneficial effect for the treated vertebrate individual. In some embodiments, it may be sufficient and even advantageous to coat only a portion of the surface with the viral particles (formulated or not in the pharmaceutical composition) of the support prior to its introduction in the treated vertebrate individual. For example, when a stent is to be coated with the viral particles, it may be advantageous to coat the surface of the stent in contact with the intima (exterior surface) and limit the coating of the surface of the stent in contact with blood circulation (interior surface) to avoid systemic dissemination of the viral microparticles.

Supports which can be modified to include the viral microparticles described herein (formulated or not in the pharmaceutical composition) are preferably solid supports which are designed to be located in a wound or in the vicinity of a wound. These supports includes, but are not limited to, dressings, fasteners, sealants, insertion tools, catheters, stents, tubes, adhesives, etc. The supports can be made of biocompatible polymers, nanomaterials and/or metal.

Once included on a support, the viral microparticles are relatively stable and the support can be stored for a couple of months without observing a substantial decrease in viral infectivity. As shown in the Examples section below, a stent coated by a fibrin gel comprising viral microparticles was stored for three months at 4° C., −20° C. or −80° C. without observing a substantial decrease in viral infectivity. If a support comprising viral microparticles is intended to be stored prior to its introduction in a vertebrate host, it may be preferred to store it at −80° C. to limit a decrease in viral infectivity.

Therapeutic Applications of Viral Microparticles

As indicated above, the viral microparticles described herein are capable of mediating therapeutic effects to favor the non-pathological/homeostatic wound healing process and/or limits pathological wound healing in a treated invertebrate individual. The viral microparticles mediate their therapeutic actions only in the direct environment in which they localize and only for a limited time window. As discussed herein, the baculovirus of the viral microparticles cannot replicate in the vertebrate host and lack the intrinsic ability to disseminate in remote areas (if they do not enter the general circulation). As such, the baculovirus can only mediate its therapeutic actions locally (in opposition to systemically or remotely) to the area in which they are introduced. As also discussed herein, the baculovirus' genome is eventually degraded in the infected host and as such can only mediate its therapeutic actions during a specific time window which allows a transient expression of the therapeutic nucleic acid molecule.

As used in the context of the present disclosure, the term "wound" refers to a site of injury or damage which causes the disruption of normal continuity of structures (such as, for example, the epithelium and/or the endothelium). In some embodiments, a wound is restricted to injuries/damages caused by physical means (the introduction of a stent in a large vessel for example). In addition, an "homeostatic wound healing" refers to a process restoration of integrity to injured tissues with cellular and extracellular matrix remodeling. Further, "a pathological wound healing" condition refers a condition in which the disorderly resolution of a scar has a pathological effect, for example, hypertrophic scarring, restenosis, neointima hyperplasia formation, etc.

The viral microparticles described herein can be, in embodiments, use to promote wound healing, prevent a condition associated with a pathological wound healing as well as alleviation of symptom(s) associated with wound healing. These expressions (promote/prevent/alleviate) refer to the ability of the method described herein or the viral particles to limit the pathological development, progression and/or symptomology of wound healing. Broadly, the therapeutic methods can encompass, in embodiments, the increase in the proliferation of some cells (for example endothelial cells), the reduction of proliferation of other cells (e.g. for example mesenchymal cells (such as fibroblasts) or muscle cells (such as smooth muscle cells or pericytes), the modulation of extracellular matrix cleavage and production and/or the modulation of inflammatory processes associated with the wound.

In order to achieve a therapeutic benefit to the treated individual, it is preferable to administer a pharmaceutically effective amount or therapeutically effective amount of the viral microparticles to the treated individual. These expressions refer to an amount (dose) effective in mediating a therapeutic benefit to a vertebrate individual It is also to be understood herein that a "pharmaceutically effective amount" may be interpreted as an amount giving a desired therapeutic effect, either taken in one dose or in any dosage or route, taken alone or in combination with other therapeutic agents.

The present disclosure thus provides a method of favoring the healing of a wound in a vertebrate individual in need thereof. In such therapeutic methods, the viral microparticles are first inserted within a wound (or in the vicinity of a wound) in a vertebrate individual. The viral microparticles can optionally be formulated in the pharmaceutical composition described herein and/or be included in the solid support. The viral microparticles are preferably located in the vicinity of the wound such that the recombinantly-engineered baculovirus can be discharged in the vicinity of their target cells and mediate the transduction of the therapeutic nucleic acid molecule in the infected host cells.

The method can be applied in any injury tissue (skin, large vessel, eye, etc.) where orderly wound healing is warranted. The methods can also be applied to any vertebrate individuals (such as mammals, and in some embodiments, such as humans), provided that their cells do not allow the replication of the genetically-engineered baculovirus.

In some embodiments, and as shown in the Examples below, it can be beneficial to use, as a therapeutic nucleic acid molecule, a molecule encoding a growth factor and may have angiogenic properties favoring angiogenesis in the vicinity of the wound. In the context of the present therapeutic methods, the term "angiogenesis" is associated with the restoration of appropriate blood supply to the wounded tissue and does also encompass favoring the endothelialization of the support that is being introduced into the treated individual. Several diseases, such as ischemic chronic wounds and in-stent restenosis, are the result of failure or insufficient blood vessel formation and may be treated by a local expansion/maturation of blood vessels. In some embodiment, the viral microparticles-containing support, by preventing ISR can also reduce the need (and in some embodiments eliminate the need) for anti-platelet therapy in treated individuals. In some additional embodiments, the viral microparticles-containing support can be used for carotid artery stenting. Further, therapeutic angiogenesis may be warranted to treat a variety of atherosclerotic diseases, like coronary heart disease, peripheral arterial disease, wound healing disorders, etc.

In some further embodiments, the viral microparticles described herein can be formulated as a topical composition (such as for example a topical cream, shampoo or conditioner). In such embodiment, the viral microparticles can be used to stimulate skin wound healing, skin regeneration and/or hair growth for example.

In yet another embodiment, the viral microparticles described herein can be used in tissue engineering applications. In such embodiment, the viral microparticles can be formulated with extracellular matrix components or a combination of different extracellular matrix components (which may or may not be biodegradable) and used in various tissue engineering applications, such as, for example, reconstructive soft and hard tissues (e.g., skin and bone).

The present invention will be more readily understood by referring to the following examples which are given to illustrate the disclosure rather than to limit its scope.

Example I—Material and Methods

The mammalian expression vector pCI and pVL1392 transfer vector were procured from Promega and BD Biosciences respectively. pCMV-XL4 mammalian expression vector carrying human hVEGF cDNA was obtained from Origene Technologies (Rockville, Md.). The pVL1392 vector and pCI vector, which harbors the pCMV promoter, were digested with BglII and BamH1 restriction enzymes. The cut out pCMV gene and digested pVL1392 vector were purified and a basic ligation reaction with T4 DNA ligase (Promega) was performed to insert the pCMV gene into the pVL1392 transfer vector by directional cloning method. The pVL 1392-PCMV construct was then linearized by Not1 enzyme digestion. It was then ligated in the similar way to the hVEGF cut out of the Not1 digested pCMV-XL4-hVEGF plasmid to form pVL1392-pCMV-hVEGF as the final transfer vector construct. The recombinant transfer vector was then transformed into the high efficiency DH5a-competent $E.\ coli$ (Invitrogen) by heat shock method for amplification. The plasmids were then purified with Qiaprep Spin Miniprep™ kit (Qiagen Sciences, MD). The recombinant hVEGF baculoviruses (BacVEGF) were generated by cotransfection of Sf9 insect cells with linearized baculovirus DNA (BD Baculogold) along with purified recombinant transfer vectors using Cellfectin™ (Invitrogen Life Technologies, Carlsbad, Calif.) transfection reagent as mentioned in earlier study (Paul A et al. 2011). The recombinant baculovirus stock (BacVEGF) was harvested 72 hours post transfection and further amplified using routine procedures. The viral titer [plaque forming unit (pfu)/ml_] of the amplified viral stock was then determined using the Baculovirus Fast Plax Titer™ Kit (Novagen, Madison, Wis.) according to the manufacturer's protocol. Similarly, baculoviruses carrying MGFP gene (BacMGFP) and no transgene (BacNull) were generated as mentioned in previous work (Paul A et al. 2011). Preparation methods for virus encapsulation: w/o/o and w/o/w. In order to encapsulate the viral particles by water-oil-water (w/o/w) double emulsion and solvent evaporation method (Matthews C B et al. 1999, Mok H et al. 1999), $5 \times 10^{13}$ pfu was resuspended in 100 μl of PBS containing 10% glycerol and 50 mg/ml BSA. This primary w/o emulsion solution was prepared by homogenizing the above mixture in 1 ml of dichloromethane (DCM) containing 50 or 100 mg of PLGA (poly(D,L-lactic-co-glycolic acid) for 1 min at 10 000 rpm using PowerGen™ Homogenizer 125 (Fisher Scientific). The resulting primary emulsion was added to 3 ml of 10% polyvinyl alcohol (PVA) and homogenized for 3 min at 14 000 rpm to form the secondary w/o/w emulsion. This solution was further agitated with a magnetic stirring bar in 10 ml of 1% PVA for 4 h to evaporate the dichloromethane. The hardened PLGA microspheres were centrifuged at 9000 g for 10 min, washed thrice with PBS and resuspended in fibrinogen solution for further experiments.

In order to encapsulate the viral particles by w/o/o double emulsion and solvent evaporation method (Lee J H et al. 2000), 5×1013 pfu was prepared as mentioned above. This primary w/o emulsion solution was homogenised in 1 ml of DCM containing 50 or 100 mg of PLGA and 1 ml acetonitrile for 1 min at 10 000 rpm. The resulting primary emulsion was added to 5 ml of corn oil containing 2% Span 80™ and homogenized for 3 min at 14 000 rpm to form the secondary w/o/o emulsion. This solution was further agitated with a magnetic stirring bar in 10 ml of corn oil containing 2% Span 80™ for 4 h to evaporate the DCM. The hardened PLGA microspheres were centrifuged at 9000 g for 10 min, washed thrice with PBS and stored temporarily at 4° C. The entire mechanism of PLGA microencapsulation of virus particles are demonstrated schematically in FIG. 1 B. To visualize and surface-characterize, the microspheres were microphotographed with scanning electron microscope (SEM; Hitachi S-4700 FE), as well as with Atomic Force Microscope (AFM) with a Nanoscope III (Digital Instruments, USA) using a silicon cantilever in tapping mode and nanoscope v 5.12r5 image analysis software. To view the inner structure of the virus-loaded microspheres, the dried PLGA microspheres were exposed to Os04 vapor at room temperature for 24 h in the presence of 1% Os04 solution, and then dipped in an epoxy matrix, cured at room temperature for 24 h and microtomed. The ultrathin cross-sections were noticed using Transmission Electron Microscope (TEM; Philips CM2OO FEG-TEM).

The encapsulation efficiency of Bac within PLGA microspheres was determined by digesting the PLGA polymer with 1 N NaOH for 24 h at 4° C. to extract the Bac particles into the aqueous solution (Mok H et al. 2007). The titer of Bac was then determined by a standard Bac titer assay. As an experimental control, another set of experiment was carried out where the free Bac were treated in the similar way with 1 N NaOH before determining the viral titer. The encapsulation efficiency was then calculated by dividing the titer of encapsulated viral particles by the initial titer of viral particle used. All experiments were carried out in triplicates. Formulation of Bac-PAMAM microparticles. PAMAM dendrimer (generation 0) with ethylenediamine core (MW: 516.68) containing 4 surface primary amino groups was procured from Sigma Chemicals and resuspended in phosphate buffered saline (PBS). The concentration of PAMAM peptide stock solution was initially adjusted to 10 μmol in PBS solution. In order to form the PAMAM-baculovirus microparticle, the solutions of the PAMAM and baculoviruses were first brought to room temperature and adjusted to desired concentrations. Then the PAMAM solution and baculovirus solution were mixed according to a desired PAMAM/virus ratio (0, 0.01 μmol, 0.1 μmol, 0.5 μmol and 1.0 μmol PAMAM molecules per 108 baculovirus). The mixture was incubated at room temperature for 30 min to form complexes, with gentle vortexing from time to time. The mixture was further centrifuged at 24 000 rpm for 45 min, and the pellet containing the heavier Bac-PAMAM microparticle was collected, leaving the unreacted excess dendrimer in the supernatant. The collected Bac-PAMAM was washed twice using PBS using the same centrifugation process. For every experiment, the preparation was freshly made.

Stent coating formulation. Firstly, the baculovirus was coated with PAMAM (0.5μηιol) and formulated in PLGA microspheres by w/o/o method. The prepared PLGA microspheres were resuspended in 5 mg/ml of bovine plasma derived fibrinogen, supplemented with aprotinin (20 μg/ml) to reduce fibrin degradation, and loaded in a 3 ml syringe with a 0.2-mm nozzle. The balloon expandable bare metal stainless steel stents with basic dimensions of 16 mm×3.5 mm (Liberie Monorail stent, Boston Scientific, Mississauga, Ontario) was first mounted on a PTFE (polytetrafluoroethylene) mandrel that was driven by a rotator. The loaded aqueous fibrinogen mixture in the syringe was then gradually drip-coated on the surface of the mounted stent layer by layer (0.2 ml of Bac loaded aqueous fibrinogen per layer). In between every layer, 0.05 ml of thrombin solution (20 U/ml) was added all over the stent surface using a micropipette with 200 μl micropipette tip and waited for 15 min to form thin fibrin gel layer. Polymerization of the fibrin occurred around the stent which completely encased the stent (FIG. 1). The stent was subsequently coated with a top layer of fibrinogen (2.5 mg/ml) cross-linked with genipin (0.045 mg/mL final) followed by polymerization with thrombin. The process resulted in a microsphere impregnated fibrin coated stent loaded with 5×1012 pfu Bac. The device was then crimped onto standard collapsed angioplasty balloon and delivered to the femoral artery. To visualize the PLGA microspheres impregnated on the fibrin coated stent surface (without the topmost fibrin/genipin layer) under fluorescence microscope (Nikon Eclipse TE2000-U), 1 mg Nile red was mixed in the PLGA/dichloromethane solution before preparing the microspheres and fabricating them on the stent. Similarly, the stents were also observed under SEM to envisage the surface topography. As control for in vitro transduction study, free virus containing fibrinogen complex were coated on the stents.

In vitro transduction via stent. The stents with different formulations were crimped on the balloon catheter and inflated in scintillation vials containing 5 ml of phosphate buffer saline (PBS) solution (pH 7.4) with 9 atm pressure. The expanded stent was incubated at 37° C. for 24 h, with constant agitation at 100 rpm. The PBS solutions containing the released viruses were collected at 12 h, 18 h and 24 h post incubation.

The 12 h incubation buffer was diluted and added at MOI of 250 to 1×106 seeded human aortic artery smooth muscle cells (HASMCs; Sciencell, Carlsbad, Calif., USA) after removing the standard smooth muscle cell media (SMCM) provided by the supplier. The 18 h and 24 h incubation buffers were similarly diluted with same dilution factor and added to HUASMCs. After incubating the cells with the stent incubation buffer for 8 h, the buffers were aspirated and replenished with complete growth medium for 24 h. After fixation, microphotographs were taken and the total cell numbers were determined per 200× magnification under bright field. GFP-expressing cells were also visually counted in the same fields, and results reported as the percentage of cells transduced (mean±SD) of at least five fields per culture in triplicate cultures.

To check the inactivation effect of serum on baculovirus present on the stent surface, the virus loaded stent with different formulations were incubated in 50% FBS or PBS for 1 h. This was followed by addition of the viruses resuspended in fresh PBS to 2×104 HASMCs per well in 96 well plate with an MOI of 250 for checking the GFP expression as mentioned above. 24 h post transduction, the fluorescein expressions per well were quantified using plate reader Victor3™ Multi Label Plate Counter (Perkin Elmer, USA) in terms of normalized percentage GFP expression. The experiments were performed with triplicates.

To check the effect of storage conditions on stent bioactivity, the stents were stored in cryovials for 3 months at different temperatures (4° C., −20° C. and −80° C.). As control, freshly prepared stent was used. After thawing, the stents were balloon expanded and incubated for 24 h in PBS solution in scintillation vials as mentioned earlier. The PBS solution was collected from the release vials and added to 2×104 HASMCs per well in 96 well plate with an MOI of 250 as mentioned above. The fluorescein expressions after 24 h were detected in plate reader and presented as normalized percentage GFP expression.

In vitro transduction via BacVegf-PAMAM loaded stent, VEGF release kinetics from transduced cells. In order to investigate the Vegf release kinetics from transduced HASMCs, three types of stents (BacVegf-PAMAM, BacVegf only and Ctrl stent with no virus) were expanded in PBS solution using balloon catheter and incubated for 24 h as illustrated earlier. The PBS solution containing the released viruses were collected and added to 1×106 HASMCs seeded per well in 6 well plate with an MOI 500. This was followed by 8 h incubation at 25° C. with subsequent replenishment of the incubated cells with fresh culture media. The conditioned media were collected on day 0, 2, 4, 9, 12 and 15 post-transduction and quantified for Vegf expression using Vegf ELISA kit (R&D Systems).

HUVEC proliferation assay. For the cell proliferation assay, 2×104 Human Umbilical Endothelial Cells (HUVECs)/well were seeded in triplicate for each sample in 96-well plates. After culturing for 8 h in standard endothelial cell media (ECM), the cells were washed twice with PBS. 0.1 ml of CM from transduced HASMCs (Day 4 CM from BacVegf-PAMAM, BacVegf only and Ctrl stent with no virus groups) with and without hVegf antibodies (Ab) along with 0.1 ml of fresh ECM without cell growth supplements were added to the corresponding set of wells. Similarly, CM from unstimulated control group mixed with fresh ECM was taken as the control group. After 3 days of culture, absorbance was measured at 490 nm using Cell Titer 96 Aqueous Non-Radioactive Cell Proliferation Assay (Promega) in a plate reader as mentioned previously (Paul A et al. 2011). This assay was also used to measure the cytotoxic effects of stent-released baculoviruses towards HASMCs.

Wound healing assay. HUVECs were seeded into six well plates and grown to confluency. After 24 h of serum starvation, the monolayer was carefully mechanically wounded with a 200 μl pipette tip. The wells were then washed twice with PBS to remove the cell debris and the seeded cells were replenished with 0.1 ml of the fresh ECM (without cell growth supplements) and 0.1 ml of the CM from different groups (CM from day 4 BacVegf, BacVegf-PAMAM and Ctrl unstimulated group), in presence or absence of 1 μg/mL Vegf antibody. Following HUVEC migration for 12 h, the cells were fixed with 4% paraformaldehyde and stained with crystal violet. The wound healing was visualized under inverted bright field microscope and microphotographs with 100× magnification were taken. The number of cells which had moved across the starting line (mean±SD; n=3) in each group was assessed and analyzed using Image J software to measure the wound healing as mentioned earlier (Paul A et al. 2011).

HUVEC Tube formation Assay. In vitro angiogenesis assay was performed using Cell Biolabs Endothelial Tube Formation Assay as mentioned elsewhere (Jiang J et al. 2011). Briefly, 50 μl of ECM gel prepared from Engelbreth-Holm-Swarm (EHS) tumor cells were added to the 96-well plate and incubated for 1 h at 37° C. to allow the gel to solidify. 2×104 cells suspended in CM from different groups (Day 4 CM from BacVegf-PAMAM, BacVegf only and ctrl stent with no virus groups), in presence or absence of Vegf antibody were seeded per well. After 18 h incubation period, media were removed and the cells were then incubated with 50 μl_of 1× Calcein AM for 30 min at 37° C. The cells were washed twice with 1×PBS and the endothelial capillary-like tube formation in each well was examined using a fluorescent microscope under 100× magnification and the HUVEC-made capillary network was analyzed by Image J software. The results were quantified as the mean relative tubule length/view field f SD, taking total tubule length/view field from control group as 100.

In vivo surgical procedures for arterial injury and stent implantation. All procedures were in compliance with the Canadian Council on Animal Care and McGill University animal use protocol, following all the ethical guidelines for experimental animals. Adult beagle dogs (Marshall Farms, North Rose, N.Y.) weighing 9.5 to 11 kg were used in this study.

One week before the surgery the animals were treated daily with aspirin (325 mg/day) along with normal 21% protein dog diet (Harlan, Montreal, Canada) to avoid thrombosis. A total of 28 stents were implanted bilaterally in deep femoral arteries of 14 dogs in a randomized, blinded fashion following denudation of the arterial endothelial wall, with contralateral arteries receiving stents from different groups. The animals were divided into three groups: fibrin coated stent loaded with microencapsulated PAMAM-BacVEGF virus [Coated (+); n=11 stents per group), fibrin coated stent loaded with microencapsulated PAMAM-BacNull virus [Coated (−); n=11 stents per group] and bare metal stent (Uncoated; n=8 stents per group). To confirm the transgene delivery and re-endothelization, animals from first two groups were sacrificed (n=3) after 2 weeks and arteries were harvested. The remaining animals were sacrificed after 6 weeks for further analysis.

On the day of the stent implantation, after subcutaneous pre-anesthetic medication with butorphanol (0.2 mg/Kg), acepromazine (0.125 mg/Kg) and atropine (0.025 mg/Kg), the dogs were subjected to general anesthesia with sodium pentobarbital (20 mg/Kg, injected intravenous via catheter along with the lactated Ringer's fluid) and endotracheal intubation for mechanical ventilation and isoflurane (2-3% along with supplemental oxygen) for anesthetic maintenance. Denudation of the arterial endothelial layer and stent implantation was performed according to the procedure performed in earlier studies (Welt F G et al. 2000 and Worsey F G et al. 1993). Briefly, the dog, placed in supine position under anesthetized condition, was administered intravenously with heparin (30 U/Kg) as blood thinner. Under sterile conditions, the superficial femoral arteries on both legs were surgically exposed and held in position by surgical clips. Continuous monitoring of blood pressure (iBP), respiration, temperature, pulse oximeter oxygen saturation (Sp02), hemodynamic and surface electrocardiograms were performed throughout the experimental procedure using patient monitoring system (Bionet Vet, QST Technologies, Singapore). The artery lumens were flushed with PBS to avoid mixture with arterial blood. On the basis of angiograms, femoral segments with comparable diameters were selected on both legs so that the stent-to-artery diameter ratio remains approximately 1.3. After an arteriotomy, a fogarty arterial embolectomy balloon catheter (Edwards Lifesciences Canada Inc, Ontario) was infused through the saphenous arteries and advanced to the two preselected femoral segments and secured with a tie as mentioned elsewhere (Newman K D et al. 1995). This was followed by severe balloon injury of the inner lumen of the artery with inflated balloon (balloon/artery ratio 1.2:1) to induce endothelial abrasion. Eventually the balloon catheter mounted stents were inflated at the sites of endothelial damage in the femoral arteries with nominal pressure (9 atm) for 1 min and was then slowly withdrawn leaving the stent in place. After stent deployment and closure of the arteriotomy site with 7-0 prolene suture, doppler ultrasound probe was used to check the vessel patency and confirm normal blood flow through of the stented arteries. The experimental animal is then extubated and administered with buprenorphine (0.02 mg/Kg, subcutaneously) analgesic for 1-2 days. 3 animals were euthanized by overdose of sodium pentobarbital (200 mg/Kg), intravenous at week 2, while the remaining at week 16.

Analysis of transgene expression—RT-PCR analysis. At week 2 post stent placement, the stented femoral arteries (n=3 stents/group) were harvested from Coated (+) and Coated (−) groups and divided laterally into three sections (proximal, mid and distal) after removing the stents. A part of the sections were used to detect hVegf transcript by RT-PCR, while the remaining parts were used for to detect the hVegf protein by immunostaining and reendothelization by staining. Similarly, sections were also collected at week 16. For detection of Vegf gene expression, total RNA was extracted from stented artery samples (stored in RNAlater™, Qiagen) using RNA Extraction kit (Qiagen) according to the manufacturer's instructions. The obtained RNA was quantified and reverse transcribed to Vegf cDNA using the Qiagen's Reverse Transcription (RT) kit following the supplied instructions. PCR amplification was performed on the reverse transcribed product using Taq DNA Polymerase (Invitrogen) and forward primer (5'CTTGCCTTGCTGCTCTACCTCC3') (SEQ ID NO: 1) and reverse primer (5'GCTGCGCTGATAGACATC-CATG3') (SEQ ID NO: 2) for hVegf gene (112-bp product). Amplifications were carried out for 25 cycles at 94° C. for 35 s (denaturation), 57° C. for 35 s (annealing), and 72° C. for 25 s (extension).

Immunohistochemical studies. For immunostaining, paraffin embedded 5 µm. sections were deparaffinised, blocked with donkey serum and incubated over night with 1:50 dilution of rabbit anti-hVegf (Santa Cruz Biotechnology Inc., Santa Cruz, Calif.) primary antibodies. On the second day, the slides were thoroughly washed with wash buffer and incubated with donkey anti-rabbit IgG-FITC (Santa Cruz Biotechnology Inc.) with 1:200 dilutions for 1 hour. The proportions and intensities of FITC-positive regions in the tissue sections, as seen under fluorescence microscope (Nikon Eclipse TE2000-U), gave a qualitative idea of the relative amount of hVegf expressed in the stented vascular tissue regions due to the transgene delivery from stent platform.

Assessment of stent re-endothelization—Evans blue staining. Two weeks after stent deployment animals were anesthetized (n=3, Coated + and −) and a portion of the harvested artery was incubated in 1% Evans blue (Sigma-Aldrich, Dublin, Ireland) for 15 min, followed by washing, fixing and examining longitudinally using image software as mentioned elsewhere (Sharif F et al. 2008).

Scanning electron microscope. Re-endothelialization was also assessed at 2 week and 16 week post implantation (n=3 each). Retrieved stents were washed with saline, fixed in 4% paraformaldehyde and longitudinally incised as above and examined using scanning electron microscopy (SEM).

Histological assessment. Stents were retrieved after twelve weeks and harvested vessels were embedded in methylmethacrylate plastic (Accel Lab Inc, Quebec, Canada and McGill SAIL Lab). After polymerization, the proximal, mid and distal sections of the stents were cut into 5 µm sections and stained with hematoxylin and eosin. Re-endothelialization was assessed directly under the microscope by a histologist blinded to treatment. Endothelial coverage was expressed as the percentage of the average lumen circumference covered by the endothelial cells (Sharif F et al. 2008).

Assessment of ISR—Angiogram analysis. Initial and follow-up angiograms were performed with fluoroscopic angiography (GE Stenoscop) using Omnipaque Iohexol contrast dye in anterior oblique projection and percent diameter stenosis at follow-up was calculated by (minimal stent diameter at follow-up/the mean diameter of the stent at full expansion)×100, using standard procedure as described elsewhere (Kornowski R et al. 1998). Sections were also used to evaluate the presence of inflammation and vessel wall injury at the stented sites of all the groups by injury and inflammation score method (Schwartz R S et al. 1992). Morphometric analysis. Retrieved vessels were embedded in methylmethacrylate plastic, cut into thin sections as mentioned earlier, and stained with elastic Van Gieson stain. All sections were examined by light microscopy and photographed to quantify the neointima formation and stenotic area using methods mentioned elsewhere (Schwartz R S et al. 1992; Schwartz R S et al. 1990).

Statistical analysis. Quantitative variables are presented as mean±Standard Deviation (SD) from independent experiments as described in the figure legends. Statistics were performed using student's t-test or one-way ANOVA by Bonferroni's multiple comparison post-hoc test. All statistical analyses were performed with Prism 5 (GraphPad Software). P value <0.05 was considered significant.

Example II—In Vitro and In Vivo Characterization of Embedded Baculovirus

Encapsulation of baculovirus in PLGA microspheres. In order to encapsulate the baculoviruses, the method of preparation and energy source required for formation of the primary emulsion were studied extensively and optimized in vitro. Bac was added to PLGA dissolved in DCM and the mixture was either sonicated or homogenized in presence or absence of BSA/glycerol. The viral titer was checked before and after encapsulation in order to measure the encapsulation efficiency. As the viral titer measures only the amount of active virus, the data represented as the amount of encapsulated virus denotes the actual number of active virus, and not the overall number which will consist of both active and inactive/disrupted viral particles. Our data, as presented in Table 1, reveals that sonication method did not increase the encapsulation efficiency; in fact, it has a deleterious effect on the viral viability compared to mechanical homogenization technique. On the other hand, homogenization technique produces the water oil emulsion in a much simpler mechanical agitation method which resulted in lesser loss of active virus. To further improve the encapsulation method, BSA/glycerol was mixed with the viruses to increase the virus stability, to enhance their steric hindrance against the harsh external shear stress during MS preparation and for better cryopreservation.

TABLE 1

Effect of PLGA MS preparation procedure on active virus encapsulation efficiency (in terms of percentage of initial loaded viral titre)

| Method | Homogenization | | Sonication | |
|---|---|---|---|---|
| | Bac | Bac + BSA/glycerol | Bac | Bac + BSA/glycerol |
| w/o/w (% pfu) | 15.5 ± 0.7 | 35.6 ± 3.1 | 10.6 ± 1.3 | 26.4 ± 4.1 |
| Diameter (μm) | 7.2 ± 2.3 | 9.8 ± 3.4 | 5.2 ± 3.4 | 5.6 ± 4.2 |
| w/o/o (% pfu) | 21.0 ± 1.1 | 41.4 ± 2.2 | 17.8 ± 1.0 | 26.8 ± 3.5 |
| Diameter(μm) | 9.2 ± 2.6 | 8.3 ± 3.2 | 5.8 ± 1.1 | 4.9 ± 2.2 |

It was then determined if the second emulsion solvent or the continuous phase can affect the encapsulation efficiency. An hydrophobic (corn oil) solvent was used for second emulsion step and compared it with standard hydrophilic (PVA) solvent. Oil was selected instead of water in order to reduce the viral loss in the second emulsion phase and subsequent solvent evaporation step. A significantly higher amount of encapsulation efficiency was noticed in the w/o/o method which confirms that there was less viral loss using oil compared to water in the continuous phase. The particle diameters were checked for every preparation which varied between 5-10 μm. Thus, as evident from Table 1, a w/o/o double emulsion procedure using mechanical homogenizer can efficiently encapsulate the baculoviruses which can be further enhanced by supplementing them with BSA/glycerol to protect the viral activity.

SEM photomicrographs were taken to confirm the formation of spherical shaped virus loaded microparticles (FIGS. 2A and 2A'), while the AFM images (FIGS. 2B i and 2B ii) identifies the regular, uniform and consistent surface topography of the microspheres. TEM images demonstrate empty and baculovirus loaded microspheres, while FIG. 2E reconfirms the successful microencapsulation procedure showing the entrapped baculoviruses in the cut section of a virus loaded PLGA microsphere.

Baculovirus eluting stent: physical characteristics and in vitro release profile. The prepared polymer coated stents containing the PLGA microspheres (by w/o/o method), mixed with Red Nile dye as tracer, were air dried and photographed to confirm that the polymeric stent was able to hold the embedded microspheres after stent expansion. FIGS. 3A and 3B shows a stent before and after coating with MS embedded fibrin layers, while the pinkish color of the stent in FIG. 3C confirms retention of the loaded MS on the stent surface post stent expansion using balloon catheter. A fluorescence image of the coated stents under fluorescence microscope (Nikon Eclipse TE2000-U) as shown in the FIG. 3D further confirms the above findings, where a uniform coating of the microspheres was seen on the stent surface. SEM images of the stents (FIGS. 3E to 3G) provided further morphological evidences on the surface characteristics of the coated stents demonstrating the uncoated bare metal stent struts (FIG. 3E), plain surface of the uniformly coated stent struts with fibrin multilayers (FIG. 3F) and evenly distributed PLGA MS embedded on the fibrin multilayered stent strut surfaces.

To determine the release kinetics of the encapsulated baculoviruses from the stent surface and modulate their release behavior, two different PLGA concentrations (50 and 100 mg/ml of DCM) were used using w/o/o emulsion method and compared with standard w/o/w method.

In both the methods the stent group with MS prepared from lower PLGA concentration showed much faster and higher percentage of viral release with time compared to the higher concentration (FIG. 3H). Moreover, w/o/o group showed significantly higher release of active virus at lower PLGA concentration than w/o/w group, 24 h post-incubation in PBS. A further decrease in PLGA concentration led to non-uniform MS formations and hence a concentration of 50 mg/ml DCM PLGA MS in the formulation protocol using w/o/o method for further studies.

Baculovirus surface functionalization with PAMAM dendrimer enhances transduction. To confirm the successful formation of Bac-PAMAM complex, zeta potential of the microparticles were measured as shown in FIG. 4A. At pH 7.4, the zeta potential of the free baculoviruses was negatively charged with a zeta potential of −13.4 mV+0.6. The positively charged PAMAM dendrimers, upon conjugation with the negatively charged baculoviruses, formed microparticles which resulted in an increment of surface charge towards positive. Bac-PAMAM (0.01) showed a zeta potential of −10.6±1.8 my, while Bac-PAMAM (0.1) showed −2.36±2.2 mv, Bac-PAMAM (0.05) showed 8.7±2.4 mv and Bac-PAMAM (1.0) showed 11.5±4.7 mv, where the values within brackets indicate the ratio of PAMAM/virus used in preparing the microparticles. This was further confirmed by measuring the particle size of the formed microparticles (FIG. 4B). Free baculovirus showed an average size of 226±17.6 nm, while Bac-PAMAM (0.01) showed a size of 228.5±30.8 nm, Bac-PAMAM (0.1) showed 588±54.1 nm, Bac-PAMAM (0.05) showed 328±29.5 nm and Bac-PAMAM (1.0) showed 289±27 nm. The significantly increased size of the Bac-PAMAM (0.05) particles compared to the free baculovirus indicates the efficient formation of Bac-PAMAM microparticles, generated by strong electrostatic interactions between baculovirus and PAMAM dendrimers. The excessively bigger size in Bac-PAMAM (0.1) group is probably because of the formation of larger aggregates and clumps of the formed complexes. To reconfirm the complex formation, TEM images the products were taken for morphological evidences. FIGS. 4C and D demonstrate the efficient binding of the rod like baculovirus with PAMAM dendrimers (0.05) leading to the formation of stable Bac-PAMAM hybrid complex.

Figure 5A:
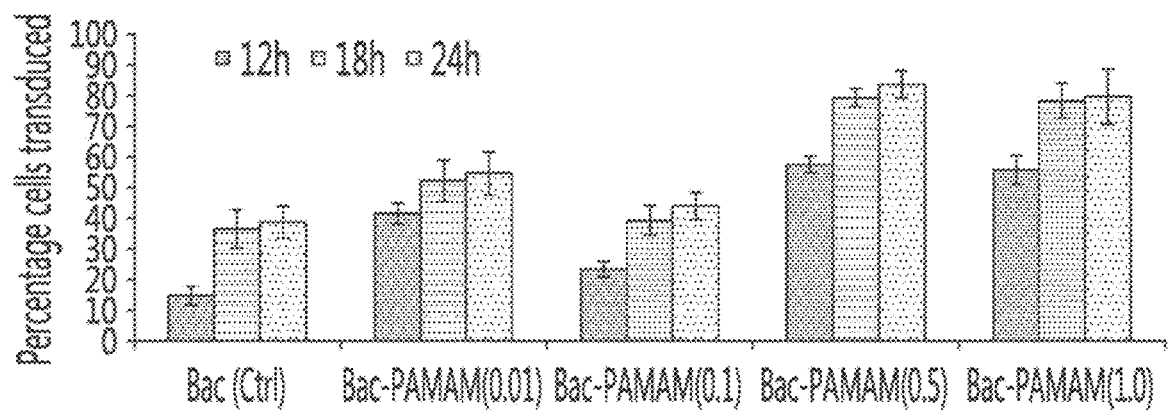
Figures 5B, 5C, 5D, 5E:
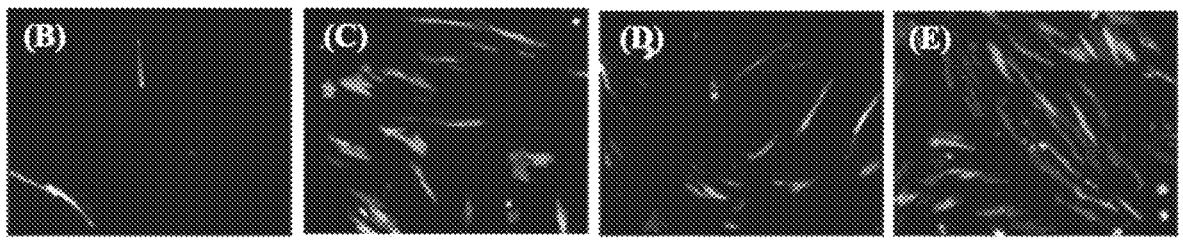
Figures 5B, 5C, 5D, 5E:
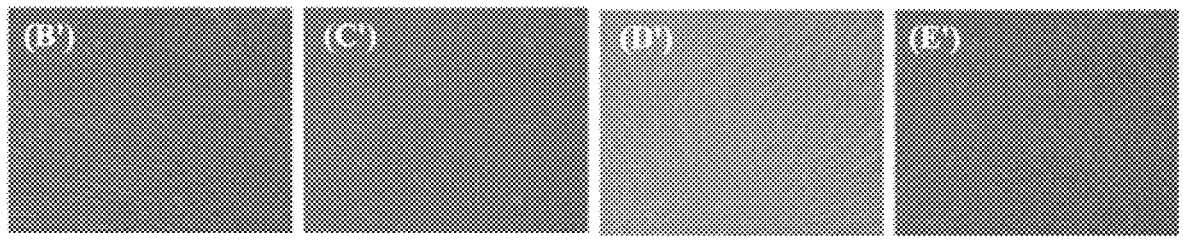
Figure 5F:
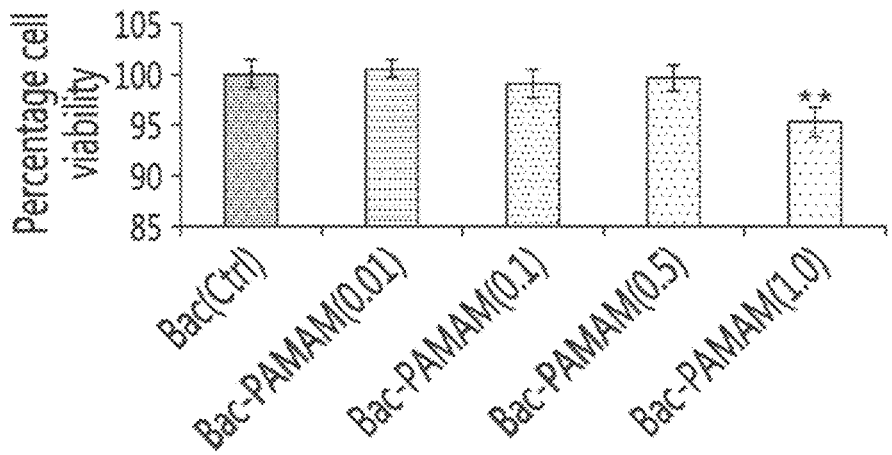

Baculovirus-PAMAM eluting stent: in vitro release, transduction and cytotoxicity analysis. To investigate whether the released BacMGFP were bioactive and can transduce the HASMCs, the incubation buffers from different release time points were collected, diluted in same proportions and added to HASMCs for transduction. After 72 h, the GFP expressions were quantified in terms of percentage cells transduced. For the study, four different baculovirus formulations using varied concentrations of PAMAM dendrimers were prepared before encapsulating and loading them on the stent surface. The data in FIGS. 5A to 5E demonstrates that PAMAM dendrimer functionalization has a positive effect on baculovirus mediated transduction with BacMGFP-PAMAM (0.5) showing consistently higher transduction efficiency than other groups, including free BacMGFP (control). Further increasing the PAMAM concentration in BacMGFP-PAMAM (1.0) however did not show any significant improvement. Moreover, the percentage of transduction was proportional to hour of incubation buffer. This is because of the higher amount of baculovirus released in the incubation buffer with higher incubation time, although there were no significant differences in transduction efficiencies between 18 h and 24 h in all groups. This indicates that the active viruses were mostly released within 12 h to 18 h from the stent. Furthermore, 72 h cytotoxicity studies on the effect of these different formulations on HASMCs show that BacMGFP-PAMAM can be safely used for cell transduction, although BacMGFP-PAMAM (1.0) group with high PAMAM concentration showed significantly high cytotoxicity compared to the control (FIG. 5F).

Effect of serum and storage condition on bioactivity of the stent. The in vivo applications of baculovirus are limited mostly because of their serum inactivation. The stents were incubated in 50% FBS for 1 h followed by incubation in PBS for 24 h. As control, 50% FBS was replaced by PBS solution. The incubation buffer was then used to transduce the HASMCs as mentioned earlier and GFP expression was detected and quantified using plate reader. FIG. 5A shows that compared to control PBS, serum has an inactivation effect in all the groups which was more distinct BacMGFP stent control group where baculoviruses were loaded directly on the stent surface without microencapsulation. In the BacMGFP MS stent group, there was much higher GFP expression compared to Bac stent in presence of serum demonstrating that the MSs were able to protect the entrapped baculoviruses against serum inactivation. However, BacMGFP-PAMAM MS stent group showed highest GFP expression and hence, highest protection against serum. This may be because of the combined effect of the MS encapsulation and PAMAM coating on the viral surface.

To further understand whether the prepared stents can be stored under different storage conditions, they were stored under different temperature conditions for long term storage of 3 months. After thawing and incubation in PBS solution, the incubation buffers were used to transduce the HASMCs as described earlier. FIG. 5B demonstrates that $-80°$ C. is ideal for long term storage compared to storage at $4°$ C. and $-20°$ C., although there was significant difference in GFP expression when these groups were compared to freshly prepared one.

Quantification and functional analysis of expressed hVegf from transduced HASMCs. Conditioned media, collected from BacVegf-PAMAM (0.5) and BacVegf transduced HASMCs at regular intervals, were used to quantify and detect the Vegf release profile using a hVegf ELISA. CM from non-transduced cells was taken as the negative control. The data, as shown in FIG. 7A, demonstrates rapid expressions of hVegf in BacVegf-PAMAM and BacVegf groups in the first 4 days which gradually decreased over the week. Although Vegf expression decreased considerably in BacVegf group after three weeks, BacVegf-PAMAM group maintained significantly higher Vegf expression.

The bioactivities of the released hVEGF in media from the BacVEGF-PAMAM (0.5) transduced HASMCs were evaluated in vitro by observing the proliferative capacity of the HUVECs. Cell Proliferation MTS Assay kit was used to assess the proliferation capabilities of the HUVECs treated with CM (containing secreted hVEGF) from experimental samples, collected on day 4 post transduction. As shown in FIG. 7B, groups BacVegf and BacVegf-PAMAM showed significantly high HUVEC proliferation on day 3 compared to unstimulated control, with BacVegf-PAMAM exhibiting the highest proliferation ($3.98±0.19×104$ cells). As expected, group treated with antibodies against hVEGF showed no proliferative effects proving that it was because of the bioactivity of released hVEGF from genetically modified SMCs that contributed to the drastic HUVEC proliferations. This proliferation rate was directly dependant on the amount of the VEGF released which explains why BacVegf-PAMAM demonstrated better results than BacVegf and unstimulated control groups.

Similar results were noticed in the wound healing assay where the abilities of CM from different experimental groups, collected on day 4 post transduction, to promote HUVEC migrations were measured. As depicted in FIG. 7C, stimulation of wounded HUVEC monolayer with CM from BacVegf-PAMAM exhibited significant healing of wounded area ($89.4±7.5%$) compared to CM from unstimulated control ($12.4±2.4%$) and BacVegf ($61.7±5.5%$). Pre-incubation of CM with the neutralizing anti-VEGF antibodies completely hindered BacVegf-PAM AM CM induced wound healing, clearly suggesting that chemotactic signals from hVEGF are required for proper wound healing effect.

In addition, the biologic activities of the CM were also evaluated by HUVEC tube formation assay. As illustrated in FIG. 6Di, cells treated with CM from BacVegf-PAMAM induced significantly enhanced effect on HUVEC capillary network formation as compared to the cells treated with CM from BacVegf and unstimulated groups. The relative tubule length was significantly enhanced in BacVegf-PAMAM and BacVegf group compared to control ($141.5±7.9$ and $100±13.6$ vs. $47±2.1$). Also, to assess the extent of impact of hVegf present in the CM on HUVEC tube formation, anti-VEGF antibody was added to the supernatant with released CM. A significantly reduced tube formation was observed which provides evidence of the strong pro-angiogenic nature of VEGF present in the CM. Similar results were also noticed when total capillary tubule numbers were quantified in BacVegf-PAMAM and BacVegf group and compared to unstimulated control ($15.5±3.4$ and $10.1±2.2$ vs. $4.5±0.7$) in FIG. 6Dii.

Figure 8B:
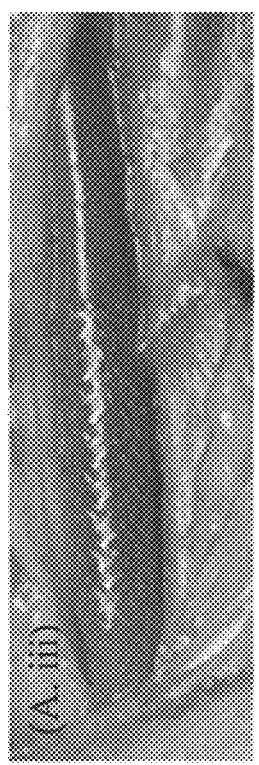
Figure 8B:
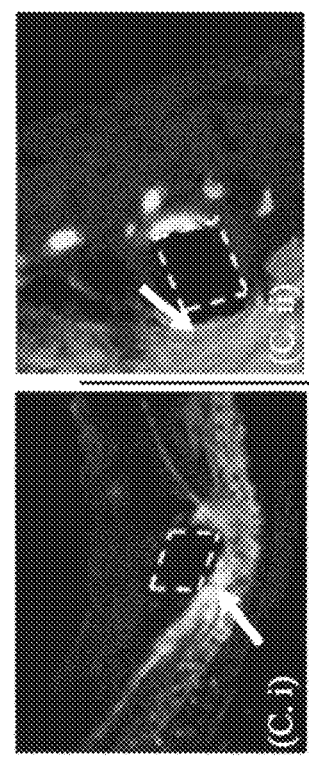
Figure 8B:
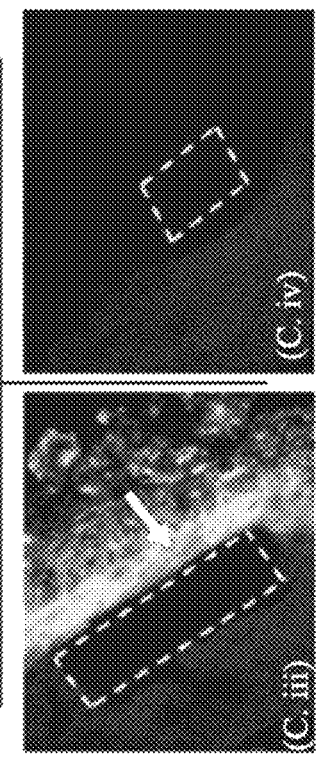
Figure 8B:
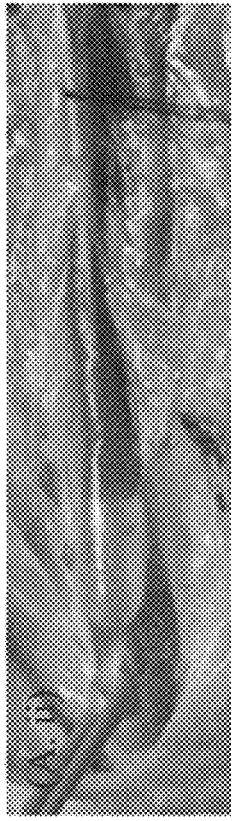
Figure 8B:
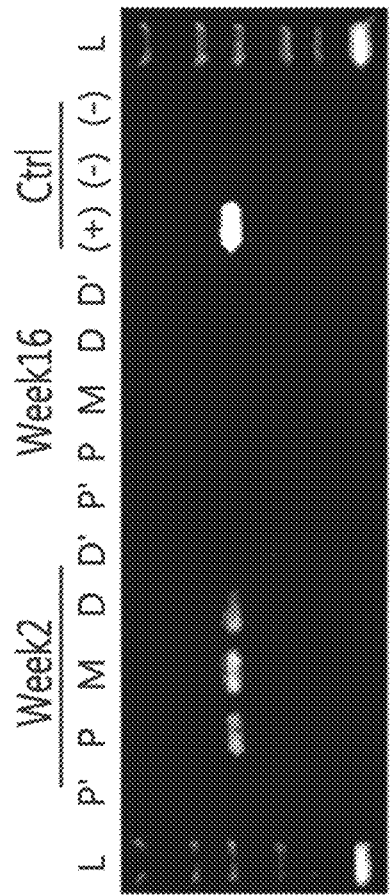

Detection and localization of Vegf expression in vivo. The in vivo stent implantation procedure has been demonstrated in FIG. 8A, where the dogs underwent bilateral femoral artery denudation by balloon angioplasty (FIGS. 8Ai and i), followed by stent deployment at the injured site (FIG. 8Aiii). Stented femoral arteries transduced with Coated (+) and Coated (−) were harvested 14 days after stent placement. Following qualitatively reverse transcriptase-PCR analysis, hVegf signal expression could be observed in all the proximal, middle and distal sections of the BacVegf-PAMAM (Coated+) transduced arteries examined (n=3 vessels), while nothing was detected in BacNull-PAMAM (Coated−) transduced arteries (FIG. 8B). Although, the RT-PCR product from 2 weeks BacVegf-transduced tissue samples demonstrated the presence of the appropriate-sized band for hVegf in the stented artery sections, no bands were detected from 16 weeks samples proving that the transgene expression is transient and disappears over time. Moreover, artery sections from 1 cm proximal and distal to the stented artery did not show any transgene expression, thus indicating that the gene delivery was localized and restricted to the stented region where the virus containing polymer coated strut touches the inner wall of the artery.

Stent-based delivery of BacVegf to the canine femoral arteries resulted in localized overexpression of Vegf. This transgene expression was localized to the areas around the stent struts in the intimal and medial layers as demonstrated elsewhere with P-galactosidase gene delivery using adenovirus and adeno-associated virus-coated stents (Sharif F et al. 2006). The expression detected on day 14 was localized near the stent strut region, mainly on the medial side where the polymer of the stent touches the arterial surface; in contrast, there was no Vegf staining observed in the stented arteries treated with Coated (−) stents.

Endothelial recovery in stented arteries. Endothelial regeneration was determined using three independent methodologies: Evan's blue staining, scanning electron microscopy and histology. Two weeks after balloon injury and stent placement, endothelial regeneration was assessed in the animals treated with BacVegf-PAMAM and BacNull-PA- MAM coated stents using Evans blue staining (n=3 stent). Luminal staining for Evans blue demonstrated that the balloon angioplasty and stenting procedure completely denuded the femoral artery in Control (−) stent while Coated (+) showed marked recovery at week 2 (FIG. 9A). As evident from FIG. 9B, re-endothelialization was significantly greater in the Coated (+) vessels (55.36±4.64%) in comparison with Coated (−) control vessels (37.5±6.51%, $P<0.05$).

Furthermore, at 2 weeks and 16 weeks after stent deployment, SEM pictures of the inner surface of the stented arteries were taken. Cells consistent with endothelial morphology were noted on the surface of BacVegf-treated stent struts on week 2, which completely covered the stent surface in a uniform way after 16 weeks (FIG. 9C). In contrast, an irregular rough surface, mainly comprising of the exposed stent strut and partially covered neointima tissues, was noticed in the arteries with BacVegf-treated stent on both week 2 and week 16.

Sixteen (16) weeks after the stent placement, histological assessment of endothelial regeneration demonstrated a significant difference in endothelial regeneration between the three groups [Coated+, Coated− and uncoated bare metal stents]. The percentage of endothelial cells observed in the Coated (+) vessels was significantly higher than in the control vessels (93.5±5.2% vs. 75.4±9.3% and 72.4±4.1; $P<0.05$) as shown in FIG. 9D.

Detection of stenotic area in stented artery: morphometric and angiographic analysis. All vessels were angiographically and histologically patent throughout the period of study. Stent malapposition was also not detected in any animal. 16 weeks after site-specific Vegf gene transfer, the stenotic area was significantly reduced in Coated (+) compared to control group stents (54.58±14.1% vs. 69.6±15.51 vs. 85.4±10.14%; $P<0.05$) as analyzed by angiography (FIG. 10). Representative photomicrographs of histologic cross sections from stented arterial segments at 4 month follow up are shown in FIG. 10. The extent of vessel injury at the stent site was similar in all the groups as determined by injury score (Coated (+) 1.13±0.14 vs. Coated (−) 1.15±0.27 vs. Uncoated 1.21±0.35). Similar results were also obtained with inflammation score (Coated (+) 0.66±0.34 vs. Coated (−) 0.7±0.31 and Uncoated 0.81±0.45; $P>0.05$).

Histomorphometric analysis (FIG. 11) demonstrated a significantly reduced intimal hyperplasia in Coated (+) group compared to other two groups (FIG. 11 E, 61.36±15.15% vs. 78.41±13.84 and 87.66±8.54%; $P<0.05$). Similar results were obtained when analyzed in terms of cross-sectional mean neointimal area (FIG. 11 E, 2.23±0.56 mm2 vs. 2.78±0.49 mm2 and 3.11±0.23 mm2; $P<0.05$). One (1) cm proximal and distal to the stented area showed no signs of intima formation.

ISR caused by intimal hyperplasia post angioplasty and stenting remains a major cause of concern and challenge for clinical investigators and researchers. To develop a therapeutic strategy which would reduce ISR by accelerating local re-endothelization at the stented site, a gene therapy was selected as it offers a promising tool for the treatment of ISR. Efficient gene therapy using suitable nanodelivery systems can induce a therapeutic effect for several days, whereas the half-life of recombinant protein and other pharmaceutics in circulation is much limited and proved to be ineffective in certain human. Although previous preclinical studies have shown promising results and clinical studies have demonstrated the safety and feasibility of vascular gene transfer in patients, none of the randomized controlled phase-II/HI gene therapy trials have shown relevant positive effects on inhibiting ISR. The reasons may be inadequate dose response effect due to low gene transfer efficacy, cell-mediated immunity to virus-transduced cells, lack of sophisticated vector delivery method or an amalgamation of several interrelated factors. Taking into account the technical and pharmacological shortcomings of previous studies, it was determined to develop a clinically relevant gene eluting stent that can successfully ameliorate the vascular biology of the stented site by promoting local endothelial recovery. Novel dendrimer coated BacVegf eluting stent were designed and developed using a composite polymer containing PLGA microspheres and fibrin biopolymer as the gene delivery platform. The results demonstrated here confirm that Vegf transgene can be effectively delivered to the vessel wall by the microencapsulated baculovirus, as detected in vivo in the transcript and protein level on day 10 post stenting. The transgene delivery not only improved early reendothelialization at the stented site but also significantly reduced neointimal proliferation as assessed by angiography and histomorphometric data at 4 months of follow-up. Prior studies have demonstrated that 4 month study period can be considered as an appropriate end point to detect vascular responses post stenting, after which the intimal response stabilizes with little change over the next 2 years.

In this work, baculoviruses were microencapsulated using a new procedure of w/o/o double emulsion to restrict viral loss to the hydrophilic phase during second emulsion, achieve high encapsulation efficiency and obtain favorable release profile of the active baculoviruses. This method proved much effective in maintaining higher encapsulation efficiency compared to earlier used w/o/w method. Baculovirus formulated in PLGA microspheres was released in two phases, where an initial burst release was noticed within 12 h of incubation followed by a slow, continuous release in next 12 h where the PLGA microspheres undergo slow degradation by hydrolysis of ester linkages to yield lactic and glycolic acid. Both mechanical homegenization and sonication induced emulsification procedures were used to entrap the viruses within the microspheres. But, sonication process reduced the encapsulation efficiency of active baculoviruses compared to that prepared by homogenization.

Recently, potential of recombinant baculovirus for angiogenic therapy in myocardially infarcted animal model using a nanobiohybrid system was reported (Paul A. et al. 2011). To extend its prospect for further angiogenic therapy applications, improvement of transduction efficiency was made by hybridizing the baculovirus with cationic hyperbranched PAMAM G0 dendrimers before microencapsulating them. The amino terminal groups of dendrimer coated baculovirus could facilitate the electrostatic interactions with negatively charged cell surface which augment viral binding to the cell surface and their subsequent entry into the cells. Our present study demonstrates that surface modifying the baculovirus with positively charged PAMAM dendrimers can also improve gene transfer efficiency. Among other widely used polymers, polyamidoamine (PAMAM) dendrimers has been shown to function as highly efficient cationic polymer vectors for gene delivery. PAMAM dendrimers are synthetic nanoparticles with a unique molecular architecture, characterized by their well defined structure, high degree of inter-molecular uniformity, low degree of polydispersity, and multiple terminal amino functional groups. Most importantly, it can be an excellent polymer for conjugation of functional molecules while maintaining low toxicity in vitro and in vivo.

Aside from improved transduction, the present work demonstrates the feasibility of encapsulating dendrimer-coated active recombinant baculovirus into microspheres in order to achieve a controlled release from polymeric stent surface with minimum cytotoxicity. Very importantly, the microencapsulated Bac-PAMAM stent also showed significantly higher protection of bioactive baculoviruses against serum inactivation compared to stents with microencapsulated Bac, and non-encapsulated Bac and Bac-PAMAM stents. Our data confirms that even PAMAM coating can also protect the Bac against serum inactivation to some extent, which is further enhanced by encapsulating them inside PLGA microspheres. The preservation of bioactivity of the stent for at least 3 months, once stored at −80° C., can be of significant logistic advantage under real life clinical settings, where the stored stent can be of immediate off-the-shelf use for any patient undergoing angioplasty and stenting without delay.

As a first step to evaluate the therapeutic potential of this newly formulated gene eluting stent, stent were loaded with Vegf carrying baculovirus and in vitro analysis were performed. So far drug-eluting stents has proved to be a useful strategy for the prevention of ISR using antiproliferative drugs like rapamycin, paclitaxel and everolimus. But recent clinical outcomes indicate that this approach is leading to incomplete endothelization and associated risk for stent thrombosis. The underpinning cause for this is that the drugs, apart from restricting the smooth muscle proliferation, impinge the natural endothelial regeneration process. Thus improving the regenerative capacity of the vessel wall endothelial cells, impaired by the antiproliferative agents, is critical to alleviate the risk of stent thrombosis and neointima formation. Earlier studies have shown that site specific arterial Vegf gene transfer lead to collateral vessel formation and increased capillary density in ischemic tissues. As a follow up work, several studies reported that exogenous balloon and stent delivered Vegf gene has the potential to accelerate thrombus recanalization and promote re-endothelization in denuded arteries. This, in turn, attenuates ISR and inhibits stent thrombosis. Our in vitro and in vivo findings are in sync with these prior findings and further focuses on advancing the gene delivery technology using optimized stent/polymer/gene combination. Here, it is illustrated that the viruses released from the microsphere embedded stent can efficiently transduce the HASMCs in culture, with BacVegf-PAMAM showing significantly higher expression of Vegf compared to that with BacVegf. In addition, in vitro functional assessment by HUVEC proliferation, wound healing and tube formation assays confirm the biological potency of the expressed Vegf protein.

Preclinical studies have confirmed the safety and efficacy of fibrin coated stents post deployment. With that knowledge, the development a biocompatible stent surface by coating the metallic stent with layers of fibrin hydrogel, impregnated with baculovirus loaded biodegradable PLGA microspheres was sought. The topmost genipin/fibrin layer serves as the barrier to external damages during crimping on the balloon catheter as well as protects the inner layers from premature virus release during its passage through the lumen of the artery at time of implantation at the desired site. The addition of genipin, as a natural cross-linker to fibrin is believed to work towards reducing the chance of any inflammatory reactions. Through the stent coating method presented here, the inner surface of the stent (i.e., the mandrel contact surface) was not coated with the polymer. Consequently, there was no fibrin coating on the blood contact side of the sten to reduce the loss of loaded viruses into the blood stream.

As illustrated in this study, the stent acted as an ideal platform for local baculovirus delivery to the stented blood vessel wall with no signs of potential inflammatory responses in the artery. Notably, the recombinant baculovirus showed a rapid expression of transgene within the first 4 days of in vitro stent mediated transduction, followed by a gradual decrease in expression level over the next two weeks. Similarly, it was observed localized in vivo Vegf transgene expression at the site of stent implantation for at least 2 weeks post deployment as evident by RT-PCR and by immunohistochemical analysis, where the later confirmed gene over-expression around the stent struts. As expected, the expression ceased when analyzed at the transcript level on week 16. This transient nature of baculovirus expression indicates that it can be advantageous in treating problems like ISR where the gene expression is no longer needed once endothelial recovery is complete. The present work proves this postulation showing complete recovery of endothelial layer is possible by temporal expression of transgene for 2-3 weeks. This observation supports previous published results, where transgene expression for just 10 days proved sufficient for complete endothelial recovery at the stented site. More importantly, this transient nature of baculovirus expression makes it a prospective gene delivery vehicle for biologically safer clinical applications compared to widely experimented mammalian viral systems.

While the disclosure has been described in connection with specific embodiments thereof, it will be understood that the scope of the claims should not be limited by the preferred embodiments set forth in the examples, but should be given the broadest interpretation consistent with the description as a whole.

REFERENCES

Jiang J, Liu W, Guo X, Zhang R, Zhi Q, Ji J, et al. IRX1 influences peritoneal spreading and metastasis via inhibiting BDKRB2-dependent neovascularization on gastric cancer. Oncogene 2011 May 23.

Kornowski R, Hong M K, Tio F O, Bramwell O, Wu H S, Leon M B. In-stent restenosis: Contributions of inflammatory responses and arterial injury to neointimal hyperplasia. Journal of the American College of Cardiology 1998 January; 31 (1):224-30.

Lee J H, Park T G, Choi H K. Effect of formulation and processing variables on the characteristics of microspheres for water-soluble drugs prepared by w/o/o double emulsion solvent diffusion method. International Journal of Pharmaceutics 2000 Feb. 25; 196(1):75-83.

Matthews C B, Jenkins G, Hilfinger J M, Davidson B L. Poly-L-lysine improves gene transfer with adenovirus formulated in PLGA microspheres. Gene Therapy 1999 September; 6(9): 1558-64.

Mok H, Park J W, Park T G. Microencapsulation of PEGylated adenovirus within PLGA microspheres for enhanced stability and gene transfection efficiency. Pharmaceutical Research 2007 December; 24(12):2263-9. Newman K D, Dunn P F, Owens J W, Schulick A H, Virmani R, Sukhova G, et al. Adenovirus-mediated gene transfer into normal rabbit arteries results in prolonged vascular cell activation, inflammation, and neointimal hyperplasia. Journal of Clinical Investigation 1995 December; 96(6):2955-65.

Paul A, Binsalamah Z M, Khan A A, Abbasia S, Elias C B, Shum-Tim D, et al. A nanobiohybrid complex of recombinant baculovirus and Tat/DNA nanoparticles for delivery of Ang-1 transgene in myocardial infarction therapy. Biomaterials 2011 November; 32(32):8304-18.

Schwartz R S, Huber K C, Murphy J G, Edwards W D, Camrud A R, Vlietstra R E, et al. Restenosis and the Proportional Neointimal Response to Coronary-Artery Injury—Results in A Porcine Model. Journal of the American College of Cardiology 1992 February; 19(2): 267-74.

Schwartz R S, Murphy J G, Edwards W D, Camrud A R, Vlietstra R E, Holmes D R. Restenosis After Balloon Angioplasty—A Practical Proliferative Model in Porcine Coronary-Arteries. Circulation 1990 December; 82(6): 2190-200.

Sharif F, Hynes S O, Cooney R, Howard L, McMahon J, Daly K, et al. Gene-eluting stents: Adenovirus-mediated delivery of eNOS to the blood vessel wall accelerates re-endothelialization and inhibits restenosis. Molecular Therapy 2008 October; 16(10): 1674-80.

Sharif F, Hynes S O, McMahon J, Cooney R, Conroy S, Dockery P, et al. Gene-eluting stents: Comparison of adenoviral and adeno-associated viral gene delivery to the blood vessel wall in vivo. Human Gene Therapy 2006 July; 17(7):741-50.

Welt F G, Edelman E R, Simon D I, Rogers C. Neutrophil, not macrophage, infiltration precedes neointimal thickening in balloon-injured arteries. Arterioscler Thromb Vase Biol 2000 December; 20(12):2553-8.

Worsey M J, Laborde A L, Miller B V, Bower T R, Landas S, Kresowik T K, et al. Endovascular Canine Anastomotic Stenting. Journal of Surgical Research 1993 January; 54(1):29-33.

wherein the viral microparticle comprises:
(i) a matrix of biocompatible biodegradable polymers; and
(ii) a genetically-engineered baculovirus having a viral genome comprising a recombinant therapeutic nucleic acid molecule, wherein the genetically-engineered baculovirus cannot replicate in the cells of the vertebrate individual, and wherein the biocompatible biodegradable polymer comprises a polyester,
and the recombinant therapeutic nucleic acid molecule encodes a vascular endothelial growth factor (VEGF).

2. The method of claim 1, wherein: the polyester comprises a poly(lactic-co-glycolic acid).

3. The method of claim 1, wherein: the genetically-engineered baculovirus is from the genera nucleopolyhedrovirus.

4. The method of claim 1, wherein the genetically-engineered baculovirus is from the subtype *Autographa californica* multicapsid nucleopolyhedrovirus (AcMNPV).

5. The method of claim 1, wherein the genetically-engineered baculovirus is a multicapsid virus.

6. The method of claim 1, wherein the genetically-engineered baculovirus is at least partially embedded in the matrix.

7. The method of claim 1, wherein the genetically-engineered baculovirus comprises a coat of cationic polymers covering at least a portion of the surface of the baculovirus.

8. The method of claim 7, wherein the cationic polymers comprise dendrimers, and optionally the dendrimers comprise poly(amidoamine) (PAMAM), and optionally the PAMAM comprises a G0 PAMAM.

What is claimed is:

1. A method of promoting the healing of a wound, or promoting re-endothelization or enhancing endothelial regeneration, in a vertebrate individual in need thereof, said method comprising placing a therapeutically effective amount of a viral microparticle in the vicinity of the wound to promote healing of the wound in the vertebrate individual, 9. The method of claim 1, wherein the viral microparticle has a relative size of at least 5 μm.

10. The method of claim 1, wherein the viral microparticle is formulated as a pharmaceutical composition, and the pharmaceutical composition comprises: (a) a gelling agent and (b) the viral microparticle.

11. The method of claim 10, wherein the gelling agent comprises a protein, a protein fragment, or both.

12. The method of claim 11, wherein the gelling agent comprises a fibrinogen, a fibrin, or both.

13. The method of claim 1, wherein the viral microparticle is embedded in or on a support.

14. The method of claim 13, wherein the support is a solid material or comprises a solid material.

15. The method of claim 14, wherein the support is metallic or comprises a metallic material.

16. The method of claim 13, wherein the support is a medical implant is or is manufactured as a medical implant.

17. The method of claim 16, wherein the medical implant is a stent.

18. The method of claim 1, comprising promoting the healing of a wound.

19. The method of claim 1, comprising promoting re-endothelization, or enhancing endothelial regeneration.

20. The method of claim 1, wherein the vertebrate individual is a human.

* * * * *